(12) United States Patent
Galvin et al.

(10) Patent No.: US 10,867,324 B2
(45) Date of Patent: Dec. 15, 2020

(54) METHODS AND SYSTEMS FOR MANAGING HEALTHCARE COSTS

(71) Applicant: MMS Analytics, Inc., Portsmouth, NH (US)

(72) Inventors: Mark Galvin, Rye, NH (US); Matthew Robinson, Stratham, NH (US); Evan Young, New Castle, NH (US); Christopher Matrumalo, Derry, NH (US); Jason Jeffords, Bedford, NH (US); Sean Kates, Portsmouth, NH (US)

(73) Assignee: MMS Analytics, Inc., Portsmouth, NH (US)

( * ) Notice: Subject to any disclaimer, the term of this patent is extended or adjusted under 35 U.S.C. 154(b) by 0 days.

(21) Appl. No.: 16/249,886

(22) Filed: Jan. 16, 2019

(65) Prior Publication Data

US 2019/0156381 A1    May 23, 2019

Related U.S. Application Data

(63) Continuation-in-part of application No. 16/101,415, filed on Aug. 11, 2018.

(Continued)

(51) Int. Cl.
| | |
|---|---|
| *G06Q 30/02* | (2012.01) |
| *G06Q 40/08* | (2012.01) |
| *G16H 10/60* | (2018.01) |
| *G06Q 10/06* | (2012.01) |
| *G06Q 10/10* | (2012.01) |

(52) U.S. Cl.
CPC ....... *G06Q 30/0283* (2013.01); *G06Q 10/063* (2013.01); *G06Q 10/06312* (2013.01); *G06Q 10/1057* (2013.01); *G06Q 30/0226* (2013.01); *G06Q 40/08* (2013.01); *G16H 10/60* (2018.01); *G06Q 30/0207* (2013.01)

(58) Field of Classification Search
CPC ................................................. G06Q 30/0283
USPC ..................................................... 705/14.11
See application file for complete search history.

(56) References Cited

U.S. PATENT DOCUMENTS

| | | |
|---|---|---|
| 7,765,117 B2 | 7/2010 | Smith et al. |
| 9,710,600 B1 | 7/2017 | Dunleavy et al. |

(Continued)

*Primary Examiner* — Azam A Ansari
(74) *Attorney, Agent, or Firm* — Kanika Radhakrishnan; Evergreen Valley Law Group

(57) ABSTRACT

Methods and systems for managing healthcare cost are disclosed. A method includes receiving, one or more employee preference inputs from an employee for accessing medical services. The one or more employee preference inputs include at least one medical service and location of the employee. The method includes accessing, a plurality of pricing from plurality of medical service providers in pre-defined region of the location. The method includes accessing, a reward program selected by an employer. The reward program includes at least reward reference percentage and a savings share percentage. The method includes determining, a reference pricing for the at least one medical service based on the reward reference percentage and the median pricing. The method includes determining, differential pricing for each medical service provider by comparing with a corresponding pricing offered. Thereafter, the method includes calculating, reward incentive based on the differential pricing and the saving share percentage.

20 Claims, 15 Drawing Sheets

Related U.S. Application Data

(60) Provisional application No. 62/544,902, filed on Aug. 13, 2017.

(56) References Cited

U.S. PATENT DOCUMENTS

| | | |
|---|---|---|
| 2004/0220836 A1 | 11/2004 | Doherty et al. |
| 2005/0027607 A1* | 2/2005 | Pearson ................. G06Q 30/02 705/4 |
| 2008/0059230 A1 | 3/2008 | Manning et al. |
| 2010/0205597 A1 | 8/2010 | Bender |
| 2012/0232936 A1* | 9/2012 | Bravata ................. G06Q 30/02 705/4 |
| 2013/0144642 A1 | 6/2013 | Bessette |
| 2014/0025471 A1* | 1/2014 | Bradley ............. G06Q 30/0226 705/14.27 |
| 2015/0248529 A1 | 9/2015 | Chen |

\* cited by examiner

| | 502 | 504 | 506 | 508 |
|---|---|---|---|---|
| | FIELD | NAME | UNITS | DEFINITION |
| 510 | ID | REWARD_INCENTIVE RECORD ID | UNIQUE ID | UNIQUE REWARD_INCENTIVE RECORD ID |
| 511 | REF_PCT | REFERENCE PERCENTILE | DOLLAR VALUE | THE PERCENTILE (AVAILABLE RANGE 50 - 150, IN 10 INCREMENTS) CHOSEN TO ESTABLISH THE BENCHMARK PRICE FOR A GIVEN PROCEDURE, WHERE 100 IS MEDIAN, 50 IS THE 25TH PERCENTILE AND 150 IS THE 75TH PERCENTILE. |
| 512 | PCT_EARNED | PERCENT EARNED | PERCENTAGE | THE PERCENTAGE OF THE "SAVINGS" (MAX ((REFERENCE PRICE - MY_MEDICAL_PRICE), 0) ) CONVERTED INTO A MY_MEDICAL_REWARD |
| 513 | MMS_SP_ID | MMS SERVICE PROVIDER ID | UNIQUE ID | MMS DEFINED SERVICE PROVIDER ID |
| 514 | PROCEDURE_CODE | PROCEDURE CODE | UNIQUE ID | MMS DEFINED PROCEDURE CODE |
| 515 | SAVINGS_OVER_REFPX | SAVINGS OVER REFERENCE PRICE | DOLLAR | REFERENCE PRICE - PROVIDER PRICE TOTAL COST OF CARE |
| 516 | EMP_REWARD | EMPLOYEE REWARD | DOLLAR VALUE | THE REWARD APPLIED TO AN EMPLOYEE'S ACCOUNT |
| 517 | FACILITY_SLUG | FACILITY SLUG | UNIQUE STRING | A UNIQUE DOT - DELIMITED STRING IDENTIFYING A FACILITY |
| 518 | PROCEDURE_SLUG | PROCEDURE SLUG | UNIQUE STRING | A UNIQUE DOT - DELIMITED STRING IDENTIFYING A PROCEDURE |

| FIELD | NAME | UNITS | DEFINITION |
|---|---|---|---|
| ID | REWARD RECORD ID | UNIQUE ID | UNIQUE REWARD ID |
| DATE | DATE | MILLISECONDS | REWARD DATE AS A UNIX TIMESTAMP IN MILLISECONDS SINCE THE EPOC |
| REF_PCT | REFERENCE PERCENTILE | DOLLAR VALUE | THE PERCENTILE (AVAILABLE RANGE 50 - 150, IN 10 INCREMENTS) CHOSEN TO ESTABLISH THE BENCHMARK PRICE FOR A GIVEN PROCEDURE, WHERE 100 IS MEDIAN, 50 IS THE 25TH PERCENTILE AND 150 IS THE 75TH PERCENTILE. |
| PCT_EARNED | PCT EARNED | PERCENTAGE | THE PERCENTAGE OF THE "SAVINGS" (MAX ((REFERENCE PRICE - MYMEDICALPRICE), 0) ) CONVERTED INTO A MYMEDICALREWARD |
| REWARD_INCENTIVE_ID | UNIQUE REWARD_INCENTIVE RECORD IDENTIFIER | UNIQUE ID | UNIQUE REWARD_INCENTIVE RECORD ID |

FIG. 5B

| FIELD | NAME | UNITS | DEFINITION |
| --- | --- | --- | --- |
| ID | REWARD PROGRAM RECORD ID | UNIQUE ID | UNIQUE REWARD_PROGRAM RECORD ID |
| START_ DATE | START DATE | MILLISECONDS | UNIX TIMESTAMP IN MILLISECONDS SINCE THE EPOC |
| DURATION_ MS | DURATION | MILLISECONDS | THE PERCENTAGE OF THE "SAVINGS" (MAX ((REFERENCE PRICE - MY_ MEDICAL_PRICE), 0)) CONVERTED INTO A MY_MEDICAL_REWARD |

FIG. 5C

| FIELD | NAME | UNITS | DEFINITION |
| --- | --- | --- | --- |
| ID | EMPLOYER RECORD ID | UNIQUE ID | UNIQUE EMPLOYER RECORD ID |
| CURRENT_REWARD _PROGRAM_ID | THE CURRENT REWARD PROGRAM ID | UNIQUE ID | THE ID OF THE REWARD PROGRAM CURRENTLY BEING USED |
| PAST_REWARD _PROGRAM_IDS | PAST REWARD PROGRAM IDS | UNIQUE ID | THE IDS OF THE REWARD PROGRAMS USED IN THE PAST |

FIG. 5D

| SERVICE NAME | DIRECTION | NAME | TYPE | STATUS | DEFAULT | DESCRIPTION |
|---|---|---|---|---|---|---|
| GET REWARD INCENTIVES | REQUEST | USER ID | STRING | MANDATORY | | THE ID OF THE USER |
| | | PROCEDURE CODE | STRING | MANDATORY | | THE PROCEDURE CODE TO GET INCENTIVES FOR |
| | | LOCATION (LON, LAT) | (LON, LAT) | OPTIONAL | EMPLOYEE'S PRIMARY ADDRESS | THE CENTER OF THE REGION THE EMPLOYEE IS SEARCHING IN |
| | | RADIUS METERS | FLOAT | OPTIONAL | 30,000 | THE DISTANCE BOUND TO SEARCH WITHIN |
| | | START TIME (MS) | INTEGER | OPTIONAL | 0 | MILLISECONDS SINCE THE EPOCH OR 0 TO GET LATEST INCENTIVES |
| | | DURATION (MS) | INTEGER | OPTIONAL | 0 | DURATION THIS INCENTIVE IS VALID FOR OR 0 IF IT DOES NOT EXPIRE |
| | RESPONSE | REWARD INCENTIVES | STRING | MANDATORY | 0 | REWARD INCENTIVES MATCHING THE REQUEST CRITERIA (EMPTY LIST WHEN NO REWARD INCENTIVES FOUND) |

FIG. 10

METHODS AND SYSTEMS FOR MANAGING HEALTHCARE COSTS

TECHNICAL FIELD

Embodiments of the disclosure relate generally to healthcare and, more particularly to, methods and systems for managing healthcare costs.

BACKGROUND

Generally, employers provide health insurance plans to their employees. Health insurance plans provided by employers may vary with regard to covered procedures, drugs, health aids, medical examinations, coverage amounts, etc. Some plans may include an annual individual and/or family deductible that needs to be satisfied before benefit payments are made. Some health insurance plans may require an insurance institution to pay a percentage of insurance amount and the remainder amount needs to be paid by the insured person. For example, a major diagnostic procedure may be paid 80% by insurance and 20% by the insured person, after the annual deductible for the insurance plan is satisfied.

There is a need to reduce the cost of healthcare and insurance. For example, employers have indicated healthcare costs are harming their businesses and growth. They generally feel powerless about healthcare and insurance costs and have noticed the level of healthcare provided affects employee retention. Employees are distracted and often overwhelmed by costs and the complexity of their healthcare and employers realize that employees don't focus on costs when the employer pays for the majority of these costs. This results in employees spending more on healthcare when the same medical services can be availed at a lower premium. In light of the above discussion, there is a need for an effective method to manage healthcare costs of employees that may mutually benefit both the employers and employees and thereby minimizing the overall expenses on healthcare.

SUMMARY

Various embodiments of the present disclosure provide method and systems for managing healthcare costs.

In an embodiment, a method of managing healthcare cost is disclosed. The method includes receiving, by a processor, one or more employee preference inputs from an employee for accessing medical services. The one or more employee preference inputs includes at least one medical service and a location of the employee. The method includes accessing, by the processor, a plurality of pricing from a plurality of medical service providers in a predefined region of the location for the at least one medical service. The plurality of pricing in the predefined region is used for determining a median pricing for the at least one medical service. The method includes accessing, by the processor, a reward program selected by an employer of the employee for the medical services. The reward program includes at least a reward reference percentage and a savings share percentage. The savings share percentage is at least a part of a savings of the employer based on a pricing for the at least one medical service. The method includes determining, by the processor, a reference pricing for the at least one medical service based on the reward reference percentage and the median pricing. The method includes determining, by the processor, a differential pricing for each medical service provider of the plurality of medical service providers by comparing the reference pricing with a corresponding pricing offered by each of the medical service providers for the at least one medical service. The method includes calculating, by the processor, a reward incentive for each of the medical service provider to be offered to the employee based on the differential pricing and the saving share percentage for the at least one medical service.

In another embodiment, a server of managing healthcare cost is disclosed. The server includes a memory configured to store instructions and a processor configured to execute the instructions stored in the memory and thereby cause the processor to perform receiving one or more employee preference inputs from an employee for accessing medical services. The one or more employee preference inputs includes at least one medical service and a location of the employee. The method includes accessing a plurality of pricing from a plurality of medical service providers in a predefined region of the location for the at least one medical service. The plurality of pricing in the predefined region is used for determining a median pricing for the at least one medical service. The method includes accessing a reward program selected by an employer of the employee for the medical services, the reward program includes at least a reward reference percentage and a saving share percentage. The savings share percentage is at least a part of a savings of the employer based on a pricing for the at least one medical service. The method includes determining a reference pricing for the at least one medical service based on the reward reference percentage and the median pricing. The method includes determining a differential pricing for each medical service provider of the plurality of medical service providers by comparing the reference pricing with a corresponding pricing offered by each of the medical service providers for the at least one medical service. The method includes calculating a reward incentive for each of the medical service provider to be offered to the employee based on the differential pricing and the saving share percentage for the at least one medical service.

In yet another embodiment, a server of managing healthcare cost is disclosed. The server includes an employer look up module for maintaining records of employees associated with an employer. The server includes one or more databases configured to store information of a plurality of reward programs offered by the employer and a plurality of medical service providers. The server further includes a pre-defined region calculator for calculating a predefined region based on an employee preference input. The employee preference input includes a medical service opted by the employee and a location of the employee where the employee wants to avail the medical service. The server includes a determiner for determining a rewards reference percentage of the employer and a savings share percentage associated with the employer. The server includes a calculator for calculating a median pricing for the medical service in the predefined region of the user. The server includes a reference price benchmark calculator for a reference pricing based at least on the median pricing and the reward reference percentage of the employer. The server includes a reward calculator for calculating a corresponding reward incentive to the employee for selecting each of a list of medical service providers present in the predefined area.

BRIEF DESCRIPTION OF THE FIGURES

For a more complete understanding of example embodiments of the present technology, reference is now made to the following descriptions taken in connection with the accompanying drawings in which:

FIG. 5A shows an example representation of a table used to store reward incentive data of an employee, in accordance with an example embodiment;

FIG. 5B shows an example representation of a table for storing rewards data, in accordance with an example embodiment;

FIG. 5C shows an example representation of a table used to store reward program data, in accordance with an example embodiment;

FIG. 5D shows an example representation of a table used to store employer data, in accordance with an example embodiment

FIG. 10 is a representation of a table indicative of a method followed by the reward incentives micro service of FIG. 9, in accordance with an example embodiment;

Figure 1:
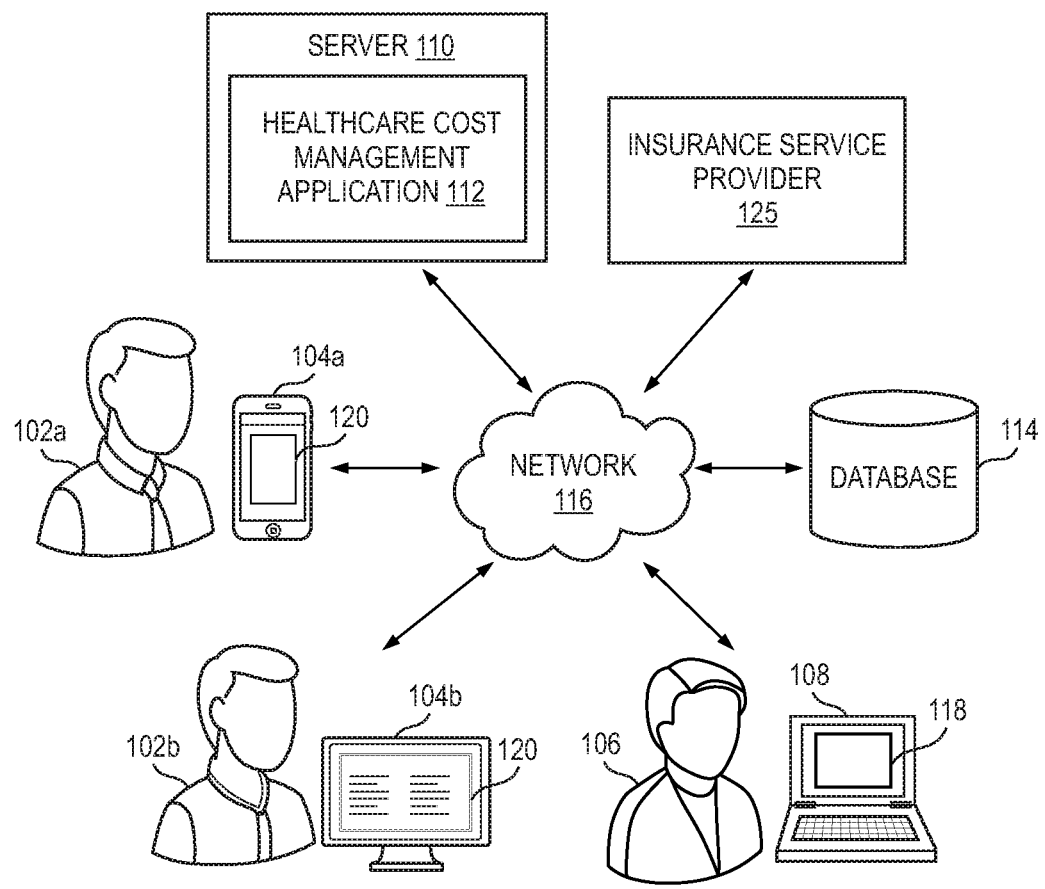
FIG. 1 is an illustration of an environment, where at least some example embodiments can be practiced.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details. In other instances, systems and methods are shown in block diagram form only in order to avoid obscuring the present disclosure.

Reference in this specification to "one embodiment" or "an embodiment" means that a particular feature, structure, or characteristic described in connection with the embodiment is included in at least one embodiment of the present disclosure. The appearance of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

OVERVIEW

Various example embodiments of the present disclosure provide methods and systems for managing healthcare costs.

An embodiment provides a method and a system for managing healthcare costs. The method includes providing healthcare management services (services) for employees by a service provider. An employer provides healthcare benefits to its employees and expects the employees to use them judiciously. The employer opts for the services and works with the service provider to set up a medical rewards program. The method followed by the service provider includes setting a reference pricing for a medical service. The reference pricing is set based on the medical rewards program of the employer, historical claim prices for that medical service in a region of the user, and statistical analysis on raw claims data. Various incentive categories are then generated based on the medical rewards program of the employer. For example, if a specific category (e.g., category X) indicates a lesser price as compared to the reference pricing, and if an employee chooses a medical service in belonging to the category X, the employee gets reward incentives based on the category X. Different categories indicate different incentives and hence, the employee gets incentives for selecting the pricing for same medical service which results in low costs for the employer. Moreover, the incentives are a function of savings of the employer. Higher the savings for medical service, higher is the percentage of savings shared by the employer with the employee. The rewards can be selected by employee and can be predefined by the employer. The rewards can be in form of points, coupons, memberships, salary or monetary perks, financial, non-financial, or any other benefit that the employer chooses to provide to employees. The rewards cumulate over a period of time and can be used by the employee to gain benefits. The rewards can be pushed into service provider system(s) or can be managed by the employer. This results in an efficient healthcare cost management system which creates a win-win scenario for all—the employee, the employer, and the service provider.

The service provider provides a medical reward incentives management application (also referred to as 'an application') which the employee and the employer can access from their mobile devices. The employer can access the application to manage the incentive reward program. The application is provided with appropriate security management to shield rewards program of one employer from other.

It must be noted that the terms 'employee' and 'insured' have been used interchangeably throughout the description and these terms refer to a person availing insurance services provided by an employer. The term 'employer' refers to an entity or a company that provides healthcare benefits to their employees. The term 'service provider' refers to an entity that partners with the employer to provide healthcare management services to the employees. The term 'medical service provider' refers to an entity that provides medical services for carrying out medical procedures. The term 'medical rewards program' refers to a rewards program set up by the employer or by the service provider or in conjunction by both as part of healthcare service offering. The term 'medical rewards incentive program' refers to that portion of medical rewards program that deal with providing reward incentives to an employee based on a pricing for the medical services availed by the employee.

The term 'reference pricing' (also referred to as 'reference price benchmark') refers to a fair price of a medical service. By choosing medical service at a medical service provider that charges less than the reference price benchmark, which is computed for every medical service availed by the employee, employees have the opportunity to earn medical reward (also referred to as 'my medical reward'). The value of the reference price benchmark can be set within the range of 50 to 150 in 10-unit increments. A value of 100 will set the reference price benchmark at the median price of the service (or procedure). In other words, exactly 50% of care for a given procedure is delivered at a price equal to or less than the reference price benchmark. The percentile (available range 50-150, in 10 increments) is chosen to establish the reference price benchmark for a given procedure, where 100 is median, 50 is the 25th percentile and 150 is the 75th percentile. The reference price benchmark can be represented by a float value in the 0.5 to 1.5 range. For example, a reference price percentile value of 110 can be represented by 1.1, and when applied to a median price of $1,000, produces a reference price benchmark of $1,100. In some embodiments, the reference price benchmark can be in percentage and the value is referred to as the reference price or benchmark price. The reference price benchmark can be calculated using employer rewards program and claims data analysis of medical claims in a user's region.

The term 'savings share percentage' refers to a proportion of the "savings" over the reference price benchmark that the employer passes on to the employee. A savings share percentage determines the proportion of the "savings" over the reference price benchmark that the employer passes on to the employee in the form of an increase to the notional balance of their health reimbursement arrangement. The value of savings share percentage can be set between 5% and 100% in 5% increments. A value of 50% will result in half of the excess of the reference price benchmark over the medical service provider's price being added to an account of the employee. The percentage of the "savings" (max ((Reference Price Benchmark−service provider's price), 0)) is converted into a reward. The savings share percentage can be represented by a float value in the 0.0 to 1.0 range.

FIG. 1 is an illustration of an environment 100 where at least some example embodiments may be practiced. The environment 100 depicts three individuals, hereinafter referred to as a user 102a, user 102b and a user 106, for illustration purposes. The user 102a (hereinafter also referred to as an 'employee 102a') is depicted to be associated with an electronic device 104a (hereinafter also referred to as a 'employee device 104a'), the user 102b (hereinafter also referred to as an 'employee 102b') is depicted to be associated with an electronic device 104b (hereinafter also referred to as a 'employee device 104b'), and the user 106 (hereinafter also referred to as an 'employer 106') is depicted to be associated with an electronic device 108 (hereinafter as referred to as an 'employer device 108'). The electronic device 104a is exemplarily depicted as a smartphone, and the electronic devices 104b and 108 are exemplarily depicted as laptops. It is understood that the electronic devices 104a, 104b and 108 of the users 102a, 102b and 106, respectively, can be any of the devices such as a mobile phone, a computer, a PDA (Personal Digital Assistant), a Mobile Internet Device (MID), a tablet computer, an Ultra-Mobile personal computer (UMPC), a phablet computer, a handheld personal computer and the like. In an embodiment, the employer 106 may decide to provide healthcare and insurance benefits to its employees and thus opts for services and works with an insurance service provider 125 to set up a medical rewards program for its employees (such as the employees 102a and 102b) who will be utilizing the healthcare and insurance benefits. The medical reward program may provide medical reward incentives to employees if they use the healthcare and insurance benefits judiciously. The employees 102a and 102b working under the employer 106 can use the medical reward programs to gain the medical reward incentives.

In at least one example embodiment, a server 110 provides a software application, referred to herein as a healthcare cost management application 112 (also referred to as 'medical reward incentives management application 112') for managing medical reward incentives and healthcare costs, in response to user requests received from the electronic devices 104a, 104b and 108 via a network 116. Examples of the network 116 include stand alone or a combination of a local area network (LAN), a wide area network (WAN), wireless, wired, any currently existing or to be developed network that can be used for communication. More specifically, an example of the network 116 can be the Internet which may be a combination of a plurality of networks.

In an embodiment, the healthcare cost management application 112 may be factory-installed on the electronic devices 104a, 104b and 108 and the users 102a, 102b and 106 may not need to specifically request healthcare cost management application 112 from the server 110. In another embodiment, the electronic devices 104a, 104b and 108 may access an instance of the healthcare cost management application 112 from the server 110 for installing on the electronic devices 104a, 104b and 108 using application stores such as Google Play store managed by Google®, Apple app store managed by Apple®, Amazon® store, and the like.

The server 110 may be a local and a physical server present at a geographical location. Alternatively, or additionally, the server 110 can be a remote server, such as a cloud based server. The server 110 may be a server associated with a third-party service provider, which provides healthcare service and manages medical rewards. Further, the server 110 may be a server associated with a third-party service provider, which provides insurance services on behalf of employers to their employees. Alternatively, the server 110 may be a server controlled by the employer, such as the employer 106. The server 110 also has access to a database 114 for storing and retrieving files used for managing medical rewards incentives or healthcare costs. The server 110 includes a memory and one or more processors. The memory includes instructions for processing data. The processor executes the instructions stored in memory and facilitates a system for managing healthcare costs to be used in an environment, such as the environment 100.

In an embodiment, the server 110 may be used for managing healthcare costs associated with providing healthcare to the users (also referred to as the 'employees'). In some contexts, managing healthcare costs may be referred to as reducing healthcare costs, maintaining healthcare consumerism, managing medical rewards, medical reward incentives, or limiting expenditures. The server 110 for managing healthcare costs associated with providing healthcare to the users may be implemented by an employer, an insurance company, or any other entity as described above. For example, an employer (such as the employer 106) seeking to manage healthcare costs associated with providing healthcare to its employees (such as the employees 102a and 102b) may use the server 110 to keep track of data pertinent to the healthcare plans of its employees.

In at least one example embodiment, the healthcare cost management application 112 is configured to manage medical reward incentives and healthcare costs using data received from the database 114 and data collected from other sources. In an embodiment, the healthcare cost or medical rewards incentives management application 112 may provide an employer interface 118 on the employer device 108 associated with the employer 106 for setting and managing the medical reward program opted by the employer 106. In some example embodiments, the employer interface 118 may provide an option to the employer 106 to set a reward reference percentage and a saving share percentage for the employees based on the reward program opted by the employer 106. In another embodiment, the healthcare cost management application 112 may provide employee interfaces 120 on the employee devices 104a and 104b. The employee interfaces 120 may be used by the employees 102a and 102b for getting medical rewards incentives based on the medical rewards program set up by their employers, such as the employer 106. The healthcare cost management application 112 may have appropriate rights management to shield rewards program of one employer from other.

In at least one example embodiment, the healthcare cost management application 112 is configured to determine a reference pricing for a medical service required by the employee, such as the employee 102a. The reference pricing sets an upper limit of what is considered a fair price for the medical service. The reference pricing is set based on medical rewards program opted by the employer 106, historical claim prices of the medical service in a region of the employee, and statistical analysis on raw claims data. In an example embodiment, the healthcare cost management application 112 is further configured to determine medical reward incentives for the employees based on the reference pricing, savings share percentage set by the employer, the statistical analysis of the raw claims data, and the service provider chosen by the employer 106.

In an embodiment, the employee interface 120 may display a list of medical service providers available in the region of the employee (e.g., the employee 102a) providing the medical service required by the employee in a decreasing order of the value of the medical reward incentive for the user/employee. The list of medical service providers may also be filtered based on additional criteria such as region, distance, and/or insurance provider. By choosing service at the medical service provider that charges less than the reference pricing, which is computed for every medical service, employees may have the opportunity to earn medical reward, also referred to as 'my medical reward'. The user/employee (e.g., the employee 102a) can choose any medical service provider from the list of medical service providers to avail medical service and the medical reward incentive for that medical service/medical service provider is determined and provided to the user (e.g., the employee 102a).

In an embodiment, the medical reward incentive earned by the user (e.g., the employee 102b) can be credited into one or more accounts associated with the user based on account prioritization set by the employer 106 and reward limits set per account as per legal constraints. A set of priority levels is used to prioritize the application of rewards to user accounts. At each priority level (say 1-4), there may be an associated account. The priority level for the accounts is defined in the reward program associated with the user (e.g., the employee 102b). The priority level determines the order in which the accounts will be credited. The reward limit is the maximum amount that can be credited into one account of the user (e.g., the employee 102b). The reward limit is decided by a government of a country in which the application 112 is used.

In an embodiment, the employer 106 can also set a reward cap using the employer interface 118. The reward cap defines the maximum reward amount that can be given to an employee, such as the employee 102a or 102b. In this embodiment, no further reward incentives will be given to the employees 102a, 102b if the received reward incentives have exceeded the reward cap.

The healthcare cost management application 112 is an application/tool resting at the server 110. In an embodiment, the server 110 is configured to host and manage the healthcare cost management application 112 and communicate with user devices, such as the electronic devices 104a, 104b and 108 for providing an instance of the application 112.

Figure 12:
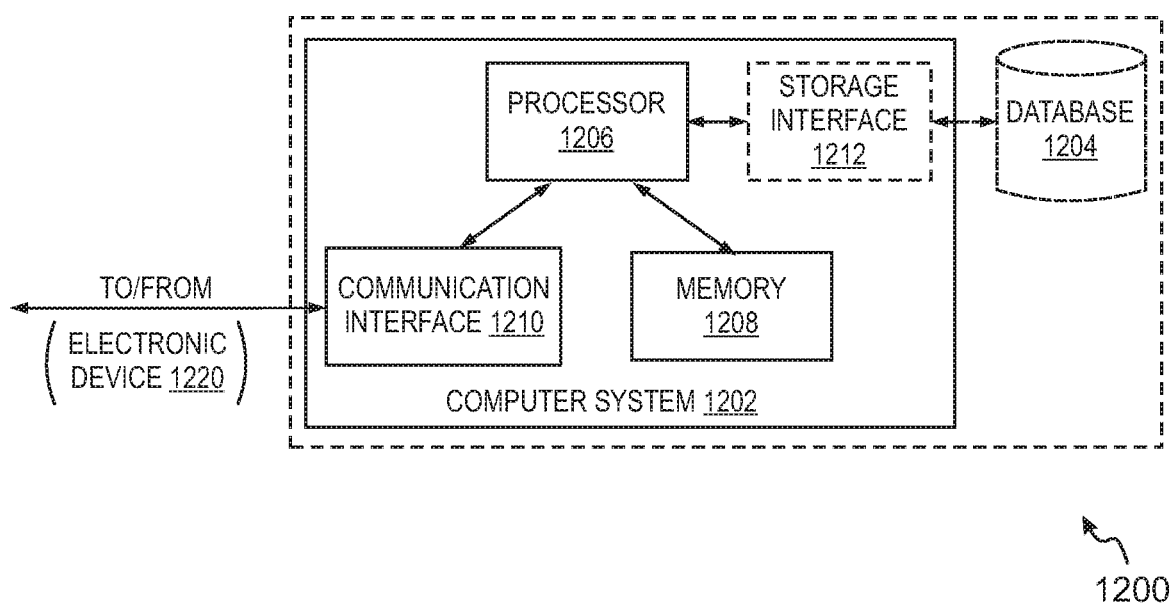
FIG. 12 is a block diagram of the server of FIG. 1, in accordance with an example embodiment.

It is noted that the instructions (or the executable code) configuring the healthcare cost management application 112 are stored in the memory of the server 110, and the instructions are executed by a processing module (for example, a single-core or a multi-core processor) included within the server 110, as is exemplarily shown with reference to FIG. 12. Accordingly, even though the various functionalities for managing healthcare costs are explained with reference to or being performed by the healthcare cost management application 112, it is understood that the processing module in conjunction with the instructions stored in the memory is configured to execute the various tasks as enabled by the instructions of the healthcare cost management application 112.

The server 110 uses localized market and plan pricing determined from raw claims data, individualized incentives (see, FIG. 6), flexible incentive program design (see, 610, 630, 632, 634, 636), employer program control, and incentives credited to health plan accounts (e.g., HSAs, HRAs, and FSAs), point systems, and non-monetary reward systems (e.g., coupons, memberships). After incentive programs are designed and selected, all program administration is automatic.

The server 110 includes various sub-processors or modules that can be implemented using one or more processors for managing healthcare costs as explained with reference to FIG. 2.

Figure 2:
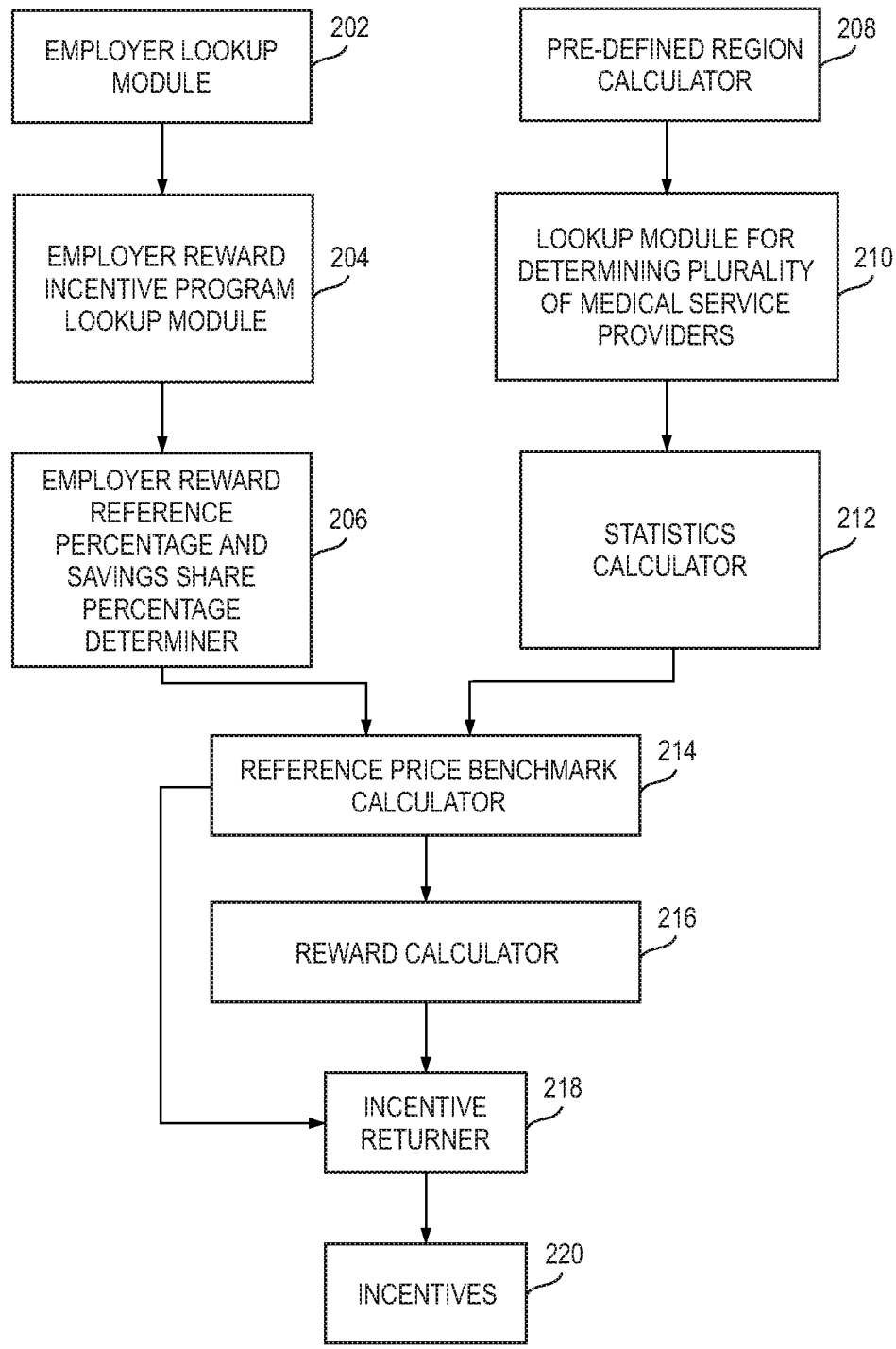
FIG. 2 illustrates a simplified block diagram of a server of FIG. 1 for determining reference pricing and reward incentives, in accordance with an example embodiment.

FIG. 2 illustrates a simplified block diagram of a process followed by the server 110 for determining reference pricing and reward incentives, in accordance with an example embodiment of the present disclosure.

The server 110 includes an employer look up module 202 which is used to determine an employer of the user (or of the employee). The module 202 can maintain records (e.g., names, IDs, employee ID, location, etc.) of all employees associated with the employer. An employer reward incentive program look up module 204 then determines the reward program of the employer. An employer rewards reference percentage and savings share percentage determiner 206 then determines the rewards reference percentage and savings share percentage either provided by the employee or a default selection of values for the rewards reference percentage and savings share percentage from the reward program selected by the employer. A predefined region calculator 208 determines a predefined region based on a location to which the user belongs, and then a look up module 210 determines a plurality of medical service providers/facilities performing medical service in the predefined region. A predefined region's medical service pricing calculator 212 calculates a median pricing for that medical service in the predefined region of the user. In an embodiment, a plurality of pricing offered by the plurality of medical service providers in the predefined region is used for determining the median pricing. The statistic calculator 212 determines minimum, maximum, mean and median values of the pricing for that medical service in the predefined region of the user.

A reference price benchmark calculator 214 then takes input from the employer rewards reference percentage and savings share percentage determiner 206 and the statistics calculator 212 and determines reference pricing as rewards reference percentage of employer*median pricing. A reward calculator 216 then calculates corresponding reward incentive for the employee for each of the medical service providers within the predefined region. A reward incentive for selecting a medical service provider is calculated as (max ((Reference Pricing−pricing of medical service provider), 0))*savings share percentage. Herein, '*' denotes multiplication. Given a reference pricing of $1,100, a pricing of medical service provider 'A' of $500, and a savings share percentage of 50%, the resulting reward incentive would be $300 (($1100−$500)*0.5=$300) for the employee.

Rewards incentives (see, 220) are then returned or outputted using an incentive returner 218 for storage and addition to the user's account.

In some embodiments, the process is followed for the plurality of medical service providers in the predefined region. Medical service providers providing the procedure(s) are selected, reward incentives calculated, and resulting rewards are sorted in decreasing order (i.e. maximum reward values are displayed first) for display to the user. It should be noted that the list of medical service providers may also be filtered based on additional criteria such as region, distance, and/or insurance provider. Based on the medical service provider selected/used by the user to obtain medical service, the rewards incentive for selecting the medical service provider is determined and provided to the user.

It should be understood that the terms "medical services or procedure" "healthcare services," "healthcare," and "medical care" are not intended to limit the scope of the present disclosure but rather may encompass all manner of medical procedures, examinations, tests, prescriptions, health aids, and emergency services.

Figure 3:
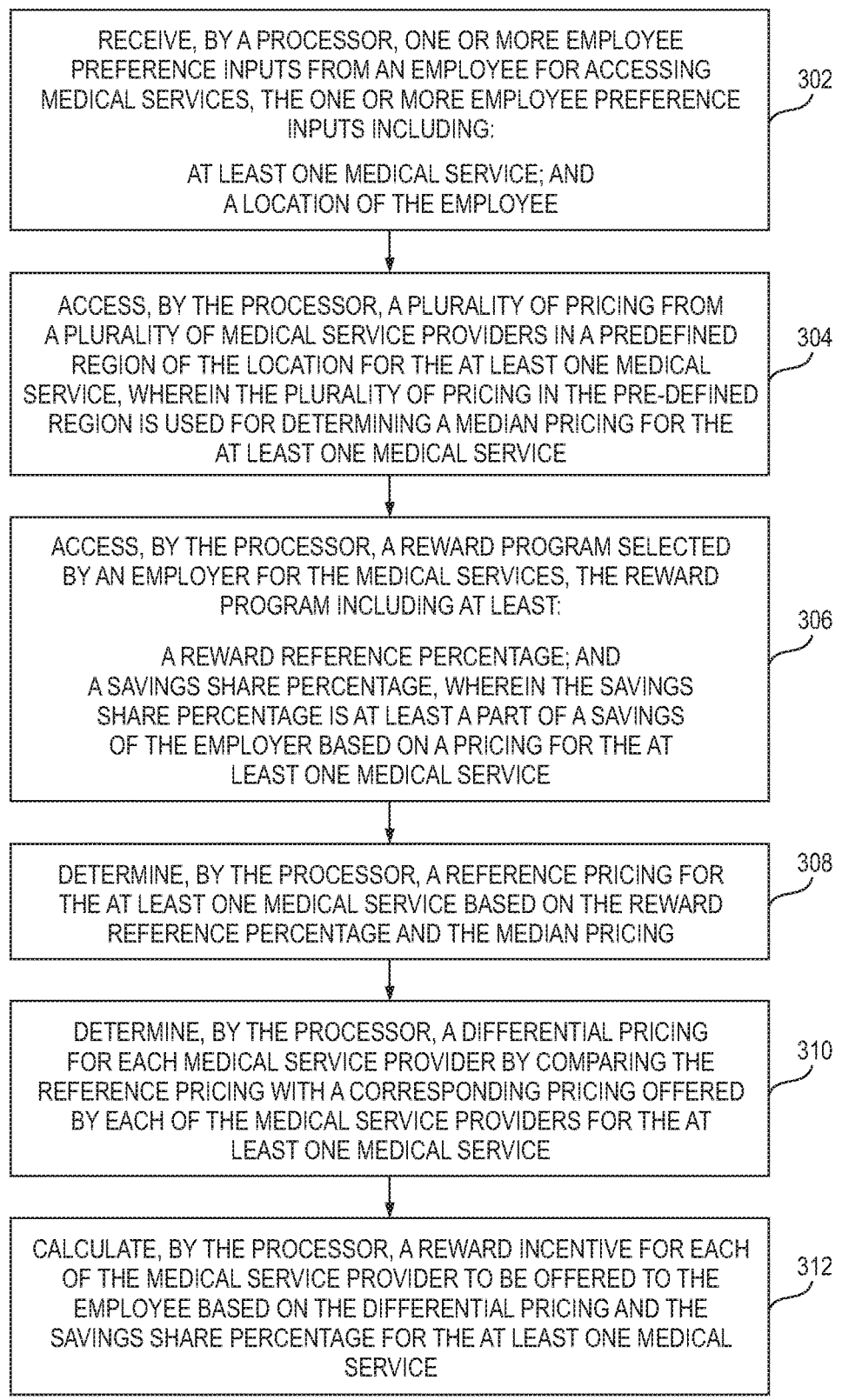
FIG. 3 is a flow diagram of a method for managing healthcare costs, in accordance with an example embodiment.

Referring now to FIG. 3, a flow diagram of a method 300 for managing healthcare costs is illustrated in accordance with an example embodiment. The operations of the method 300 may be carried out by a server such as the server 110 or the electronic devices 104a, 104b and 108. The sequence of operations of the method 300 may not be necessarily executed in the same order as they are presented. Further, one or more operations may be grouped together and performed in form of a single step, or one operation may have several sub-steps that may be performed in parallel or in sequential manner.

At operation 302, the method 300 includes receiving, by a processor, employee preference inputs from an employee for accessing medical services. The one or more employee preference inputs include at least one medical service and a location of the employee. The employee may access an employee interface (see, 120 in FIG. 1) of the healthcare cost management application 112 to provide information pertaining to the medical services required by the employee at a specific location. In an embodiment, the employee may either provide a current location and search for medical service providers in the vicinity or provide a preferred location for availing the medical services. In an example scenario, the employee may have met with an accident and an associate of the employee may search for emergency services providing medical services, for example, orthopedic and neurology services in a proximity/vicinity of an accident zone.

At operation 304, the method 300 includes accessing, by the processor, a plurality of pricing from a plurality of medical service providers in a predefined region of the location for the at least one medical service. The plurality of pricing in the predefined region is used for determining a median pricing for the at least one medical service. In at least one example embodiment, the employee may set a certain region/radius; say 2 miles as limit for defining the predefined region on the employee interface. Upon receiving the employee preference inputs, the plurality of medical service providers providing medical services (e.g., orthopedic and neurology services) are identified in the predefined region. For example, medical service providers P1, P2 and P3 may be providing orthopedic and neurology services in the region. The pricing offered by the medical service providers P1, P2 and P3 are retrieved. In an example scenario, an average pricing for accident treatment including orthopedic and neurology services may cost $1000 at medical service provider P1, $1500 at medical service provider P2 and $2000 at medical service provider P3. The median pricing is an average of the pricing offered by medical service providers in the predefined region. In this example representation, the median pricing is determined as $1500.

At operation 306, the method 300 includes accessing, by the processor, a reward program selected by an employer for the medical services. The reward program includes at least a reward reference percentage and a saving share percentage. The savings share percentage is at least a part of a savings of the employer based on a pricing for the at least one medical service. In at least one embodiment, the employer can select a reward program from a plurality of available reward programs. Each reward program may have a different scheme of determining rewards based on employer preferences, such as reward reference percentage, savings share percentage. In an example, the employer may be presented with a choice to choose from reward programs R1 and R2 that are offered to the employees. Each of the reward programs R1 and R2 may offer different benefits for the employer and the employee. For example, a reward program R1 may offer a savings share percentage of 10% with a reward reference percentage of 70% for every medical service availed below a reference pricing, whereas another program R2 offers a savings share percentage of 25% with a reward reference percentage of 85%.

At operation 308, the method 300 includes determining, by the processor, a reference pricing for the at least one medical service based on the reward reference percentage and the median pricing. The reference pricing is a fair price for the required medical service, and in an example the reference pricing can be calculated based on the formula:

Reference pricing=Reward reference percentage*Median pricing.

The rewards reference percentage is determined from the reward program selected by the employer and the median pricing is the median price for the medical service based on the pricing of service providers P1, P2 and P3 in the predefined region of the location of the employee requesting the medical service. If the employer has selected reward program R1, reward reference percentage is 70% and with a median pricing of $1500 in the predefined region, the reference pricing for the orthopaedic and neurology services will be $1050.

At operation 310, the method 300 includes determining, by the processor, a differential pricing for each medical service provider by comparing the reference pricing with a pricing offered by each of the medical service providers for the at least one medical service. The reference pricing is compared against pricing offered by each medical service provider P1, P2, P3 to determine differential pricing of d1, d2, d3. As an example, d1 is $50 for P1, d2 is $450 for P2 and d3 is $950 for P3.

At operation 312, the method 300 includes calculating, by the processor, a reward incentive based on the differential pricing and the saving share percentage for the at least one medical service. The reward incentive for the employee is calculated for each of the medical service providers P1, P2 and P3 in the predefined region using a predefined mathematical expression:

Reward incentive=(max ((reference pricing−pricing of medical service provider), 0))*saving share percentage.

Herein, '*' represents the multiplication. The saving share percentage represents the proportion of savings over the reference pricing that the employer wants to pass on to the employee. The saving share percentage is determined from the reward program chosen by the employer of the user. For example, the reference pricing is $1050, a savings share percentage is 25%, and the pricing of the medical services (orthopedics and neurology) for a medical service provider P1 is $12.5 (based on mathematical expression: max (($1050−$1000),0)*0.25=12.5). Therefore, if the employee selects medical services offered by the service provider Pl, the employee will receive a reward incentive of $12.5 for choosing the medical service at price less than the reference pricing of $1050. Alternatively, selecting services of service provider P3 with a pricing of $2000 may result in a reward incentive of $0 (based on mathematical expression: max (($1050−$2000),0)*0.25=0).

Figure 4A:
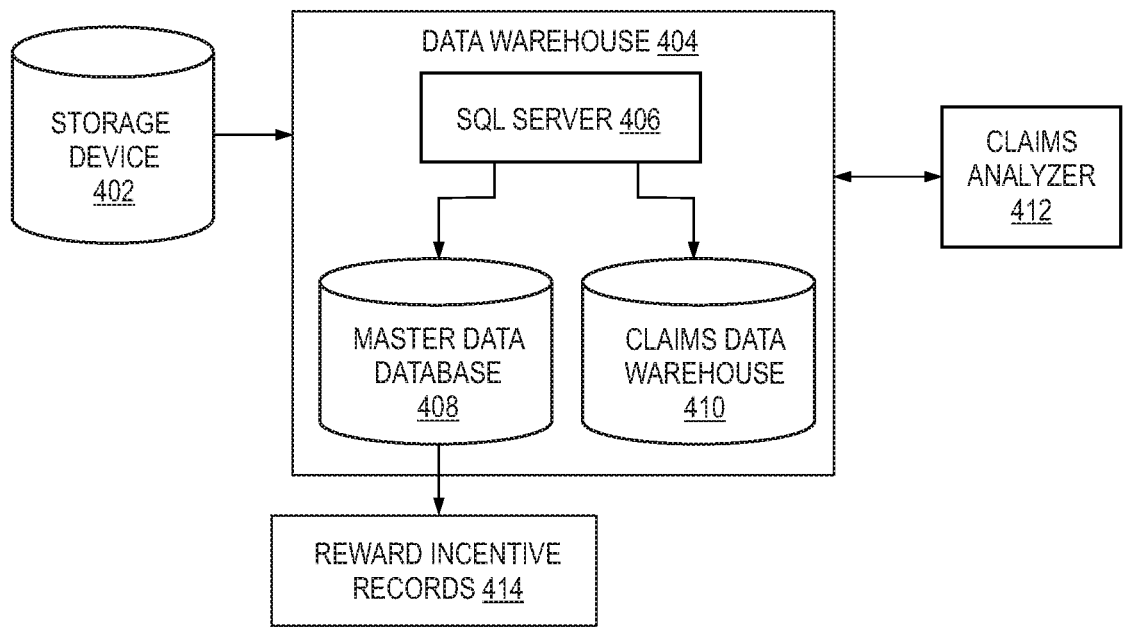
FIG. 4A illustrates a simplified block diagram of the server of FIG. 1 for generating rewards incentive and maintaining rewards incentive records, in accordance with an example embodiment.

FIG. 4A illustrates a simplified block diagram 400 of the server 110 for generating rewards incentive and maintaining rewards incentive records, in accordance with an example embodiment of the present disclosure. The server 110 includes a storage device 402, a data warehouse 404, a claims analyzer 412 and a reward incentive record 414. The data warehouse 404 includes a SQL server 406, a master data database 408 and a claims data warehouse 410.

In at least one example embodiment, the storage device 402 includes raw claims data. The raw claims data is extracted from many different sources (e.g. research data sets, insurance providers, explanation of benefits (EOB) data, etc.) and is placed in the claims data warehouse 410 as a series of rows (or lines) describing procedures performed. Each claim may be composed of several lines indicating several procedures performed. The raw claims data is disaggregated, analyzed, and baseline medical procedure price is calculated for each medical service provider providing the medical service. In an embodiment, the baseline procedure prices are determined by selecting 'final' claims (i.e. claims that have been approved and paid), aggregating National Provider Identifiers (NPIs) for a single facility when that facility bills pass through several NPIs, applying modifiers to separate professional components of procedures to be evaluated separately, and removing outliers by price based on the log transformation of prices. Once the above steps are performed, a median price is calculated for the remaining data and this price becomes the baseline procedure price for the associated medical service provider providing the medical service requested by the user.

In an embodiment, the claims analyzer 412 is configured to derive data from the claims data. The derived data includes, but is not limited to, procedures, procedure prices, and likely procedure groupings. A typical (example) set of claims analysis processes are:

Identification of unique providers and the assignment of a unique identifier to each provider Identification of unique payers and the assignment of a unique identifier to each payer Identification of lines billed as the professional component and the assignment of an identifier to analyze these procedures separately from the technical components of the same procedure Calculation of Per Member Per Month (PMPM) costs by payer Calculation of the global median for each provider/procedure combination meeting our minimum cell size policy (10 records) for a comparison with payer-specific prices Calculation of the median price for each payer/provider/procedure combination for fully insured and self-insured insurance schemes Stratification of price differences between the global procedure median and the prices calculated in the previous process by procedure category, provider type, provider location, demographics, and other factors to identify patterns of higher/lower prices for each payer and/or insurance schemes The results of claims analysis performed by the claims analyzer 412 are stored in the master data database 408. The results can also be referred to as reward incentives or reward incentive records 414. In some embodiments, reward incentive records 414 for procedures can be pre-calculated when baseline pricing is also pre-calculated. This may be the case when a blended rate for a region has been determined. Additionally, reward incentives may also be calculated on-demand based on factors such as region, plan design, and individualized preferences.

The rewards incentive data or records 414 are accessible to the healthcare cost management application 112 running on the server 110 and user devices (e.g., the electronic devices 104a, 104b and 108). In some embodiments, the reward incentive records 414 may be loaded from the master data database 408 to another storage device directly accessible by the healthcare cost management application 112 present on the user device (e.g., devices 104a, 104b, 106). The transfer and storing of the reward incentive record can be managed using the SQL server 406. The data model 450 that supports reward incentive records 414 or data is now explained in conjunction with FIG. 4B and FIGS. 5A-5D. The databases and storage device as shown in FIG. 4A are part of or connected to the database 114 of FIG. 1.

Figure 4B:
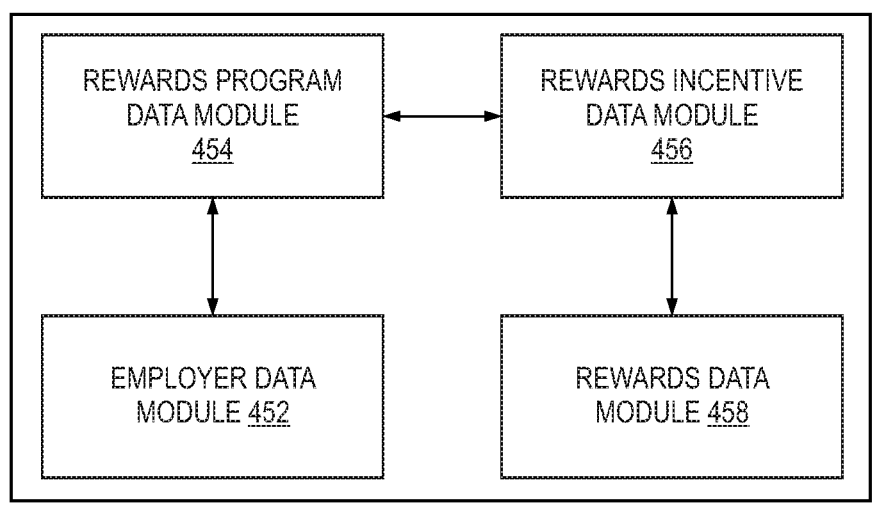
FIG. 4B illustrates a data model of the server of FIG. 1 for managing rewards incentive records, in accordance with an example embodiment.

FIG. 4B illustrates a data model 450 of the server 110 for managing rewards incentive records, in accordance with an example embodiment of the present disclosure. The data model 450 includes an employer data module 452, a rewards program data module 454, a rewards incentive data module 456, and a rewards data module 458.

The employer data module 452 organizes and maintains employer data related with employers using the healthcare cost management application 112. In an embodiment, the employer data includes information about a reward program selected by a employer, reward programs employed previously, records of employees working under each employer, healthcare claims availed by each employee so far, etc. A table used for managing employer data is explained in detail with reference to FIG. 5D.

The rewards program data module 454 is configured to maintain reward program data related with a plurality of reward programs. Each reward program may include reward program information such as, start date of the reward program, validity of the reward program, a reward cap defining a maximum limit of reward incentive, a reward reference percentage and a savings share percentage provided as reward incentive for the employee. An example of a table used for managing reward program data is explained in detail with reference to FIG. 5C.

The rewards incentive data module 456 is configured to maintain reward incentive data based on reward incentives earned by each employee over a predefined period, say, past financial year. Additionally, the rewards incentive data module 456 maintains information of a plurality of accounts linked with an employee earning the reward incentive. The reward incentive can be monetary, point based, prize/lottery based, etc. The monetary rewards are applied to one or more of the plurality of accounts such as a Health Reimbursement Arrangement (HRA), a Flexible Spending Account (FSA) and a Health Savings Account (HSA) while other rewards are defined and awarded via incentive programs. Further, the rewards incentive data module 456 also stores definition of credit limit of each account of the plurality of accounts and rules that correspond to ways in which reward can be utilized from each account by the employee. A table used for managing reward incentive data is explained in detail with reference to FIG. 5A.

The rewards data module 458 is configured to maintain reward data based on rewards earned by the employees. The rewards data includes information about an identifier for the reward earned by the employee, a reference percentile set by the employer, a reward date, reward incentive earned for a medical service, reward earned by the employee, etc. A table used for managing reward data is explained in detail with reference to FIG. 5B.

FIG. 5A shows an example representation of a table 500 used to store reward incentive data of an employee, in accordance with an example embodiment. The table 500 includes reward incentive data managed by the rewards incentive data module 456 of the server 110. The table 500 includes a field section 502, a name section 504, a units section 506 and a definition section 508. The fields section 502 represent data fields of the table 500 and columns 504, 506, 508 define/describe a corresponding data field represented in the fields section 502. The fields section 502 includes data fields for rewards record identifier represented by 'ID' (see, row 510), the reward reference percentage (available range 50-150, in 10 increments) chosen to establish the reference price benchmark for a given procedure/medical service represented by 'REF_PCT' (see, row 511), the percentage of savings defined by a predefined mathematical expression as:

$$\max((\text{Reference Price Benchmark} - \text{service provider's price}), 0).$$

The percentage of savings (represented by the predefined mathematical expression) is converted into reward by multiplying with a saving share percentage represented by 'PCT_EARNED' (see, row 512). The fields section 502 further includes information related to the medical service provider and a medical service/procedure availed by the employee. The medical service provider providing the medical service for the employee is associated with an identifier represented by 'MMS_SP_ID' (see, row 513), a medical service/procedure identifier represented by 'PROCEDURE_CODE' (see, row 514). A saving for the employer upon the employee choosing a medical service provider providing a medical service below the reference pricing. The savings is determined by subtracting the pricing provided by the medical service provider from the reference pricing represented by 'SAVINGS_OVER_REFPX' (see, row 515), rewards applied to an employee's account represented by 'EMP_REWARD' (see, row 516), unique identifier for medical service provider represented by 'FACILITY_SLUG' (see, row 517) and unique identifier for medical service represented by 'PROCEDURE_SLUG' (see, row 518).

FIG. 5B shows an example representation of a table 520 for storing rewards data, in accordance with an example embodiment. The table 520 includes rewards data managed by the rewards data module 458 of the server 110. The table 520 includes a field section 522, a name section 524, a units section 526 and a definition section 528. The field section 522 represent data fields of the table 520 and columns 524, 526, 528 define/describe a corresponding data field represented in the fields section 522.

The field section 522, in various illustrated rows 530, 532, 534, 536 and 538, respectively, includes fields for rewards record identifier represented by 'ID', reward date on which reward is earned by the employee represented by 'DATE', the reward reference percentage (available range 50-150, in 10 increments) chosen to establish the reference pricing for a given procedure represented by 'REF_PCT', the percentage of savings (max ((Reference Price Benchmark−service provider's price), 0)) converted into reward by multiplying with saving share percentage represented by 'PCT_EARNED' and a unique identifier for reward incentive earned by the employee represented 'REWARD_INCENTIVE_ID'. As an example, the row 530 depicts the data field 'ID' represented/identified by name as 'REWARD RECORD ID' and units for representation with a unique ID (e.g., 2018AB1955) and defined as a unique reward ID for rewarding employees.

FIG. 5C shows an example representation of a table 540 used to store reward program data, in accordance with an example embodiment. The table 540 includes reward program data managed by the rewards program data module 454 of the server 110. The table 540 includes a field section 542, a name section 544, a units section 546 and a definition section 548. The fields section 542 represent data fields of the table 540 and columns 544, 546, 548 define/describe a corresponding data field represented in the fields section 542.

The table 540 includes fields for rewards record identifier represented by 'ID', start date of the reward program set by the employer represented by 'START_DATE', and duration of the reward program represented by 'DURATION_MS', as illustrated in rows 550, 552 and 554, respectively. As an example, the row 550 depicts the data field 'ID' represented/identified by name as 'REWARD PROGRAM RECORD ID' and units for representation with a unique ID and defined as a unique reward program record ID.

FIG. 5D shows an example representation of a table 560 used to store employer data, in accordance with an example embodiment. The table 560 includes employer data of the employer data module 452 of the server 110. The table 560 includes a field section 562, a name section 564, a units section 566 and a definition section 568. The fields section 562 represent data fields of the table 560 and columns 564, 566, 568 define/describe a corresponding data field represented in the fields section 562. The table 560 includes fields for employer identifier represented by 'ID', current reward program identifier of a reward program selected by the employer represented by 'CURRENT_REWARD_PROGRAM_ID' and past reward program identifier of the reward program employed by the employer previously for rewarding employees represented by 'PAST_REWARD_PROGRAM_IDS', as illustrated in rows 570, 572 and 574, respectively. As an example, the row 570 depicts the data field 'ID' represented/identified by name as 'EMPLOYER RECORD ID' and units for representation with a unique ID and defined as a unique employer record ID.

Figure 6:
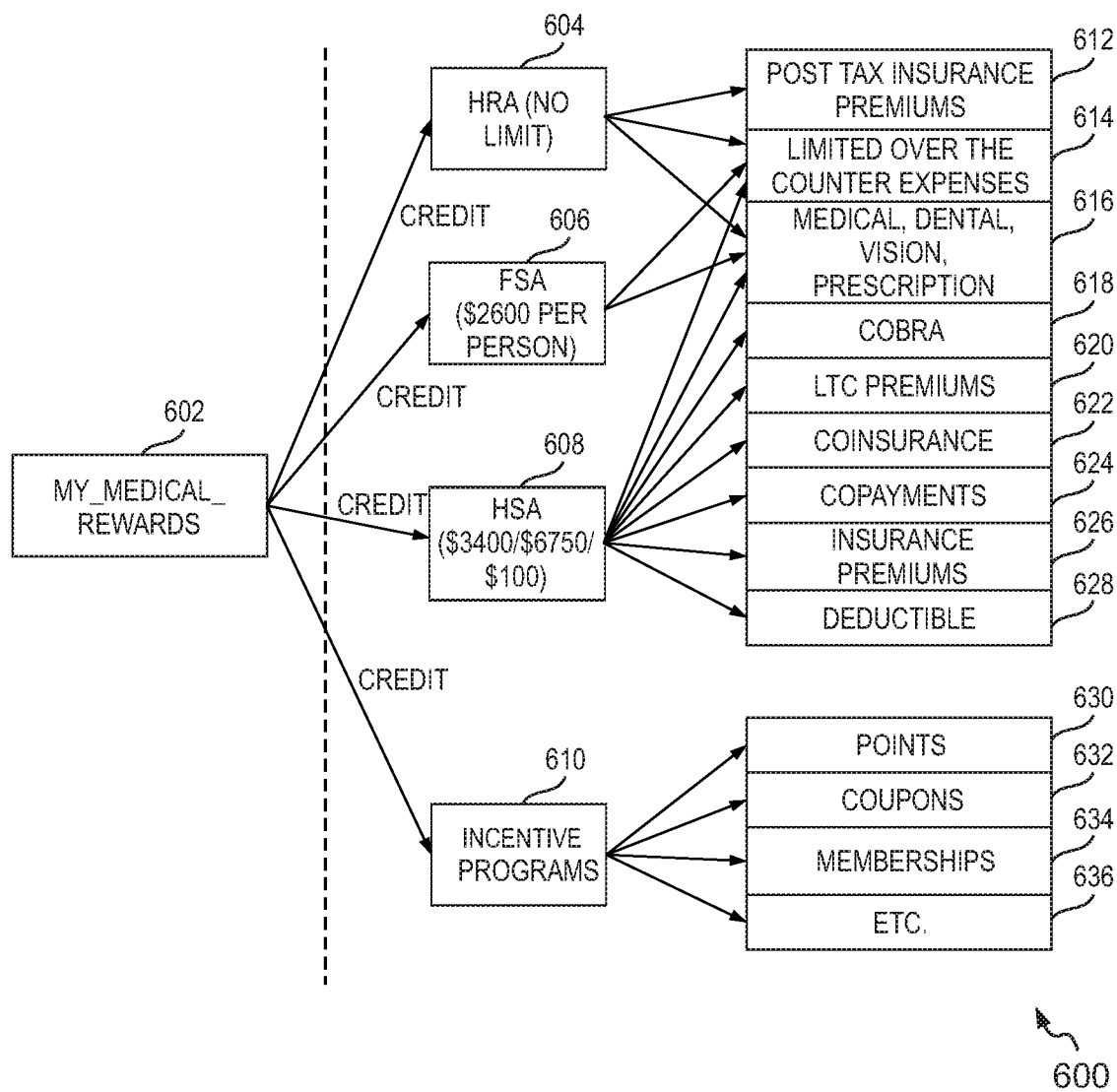
FIG. 6 shows an example representation of a rewards incentive design, in accordance with an example embodiment.

FIG. 6 illustrates an example representation of a reward incentive design 600, in accordance with an example embodiment of the present disclosure. The reward incentive design 600 is designed to reduce an overall cost for the employer while improving outcomes. The reward incentive design 600 includes a plurality of accounts linked with an employee earning rewards for using medical services below a reference pricing thereby resulting in costs savings for the employer. The reward incentive design 600 also includes credit limit for each account of the plurality of accounts and rules/ways in which reward can be utilized from each account by the employee.

In an embodiment, a reward 602 (also referred to as 'my medical rewards 602') can be monetary, point based, prize/lottery based, etc. The monetary rewards are applied to a Health Reimbursement Arrangement (HRA) (see, 604), a Flexible Spending Account (FSA) (see, 606), and/or a Health Savings Account (HSA) (see, 608) accounts while other rewards are defined and awarded via incentive programs (see, 610). An employer can design their own reward program by selecting the reward types, reward ratios, reward increments, reward priorities, reward caps, etc. For example, an employer may decide they want to grant rewards in $5 increments based on 50% of the savings on a medical service/procedure when compared with a reference pricing. Next, they want the reward to be credited to the FSA first (up to a cap) and then to be rewarded to the HSA (after the cap is exceeded). The design 600 supports flexible rewards program designs.

In the illustrated representation, the HRA 604 has no limit i.e. HRA account of the employee can be credited with unlimited amount of rewards. The HRA 604 further provides options of post tax insurance premiums 612, limited over the counter expenses 614, and medical, dental, vision prescription 616 which means post tax insurance premiums 612, limited over the counter expenses 614, and medical, dental, vision prescription 616 can be paid from the HRA account. The FSA 606 has a limit of $2600 i.e. only $2600 can be credited into FSA account linked to the employee and if the limit of $2600 is already reached, no more rewards can be credited into the FSA account. The FSA 606 further provides options of limited over the counter expenses 614, and medical, dental, vision prescription 616 which means limited over the counter expenses 614, and medical, dental, vision prescription 616 expenses can be paid from the FSA account of the employee.

The HSA 608 provides options of the limited over the counter expenses 614, the medical, dental, vision prescription 616, COBRA 618, LTC premiums 620, Coinsurance 622, Copayments 624, insurance premiums 626, and deductible 628 which means all these expenses can be paid from the HSA account. The incentive programs 610 further include options of points 630, coupons 632, memberships 634, and other options mentioned as etc. 636.

The monetary rewards are calculated and applied to one or more of the HRA 604, the FSA 606, and the HSA 608 accounts while non-monetary rewards are calculated and applied to one or more incentive programs 610. Both monetary and non-monetary rewards may be earned over a time period by an employee. The rewards may be calculated and outputted in a data export format (e.g., csv, json, etc.) for import into other systems or updated directly within other systems.

It is to be appreciated that the illustrated plan design 600 is an example and many different plan designs exist. The major components of any plan are deductible (in network and out of network) for example the FSA 606, the HRA 604, and the HSA 608 accounts and their interactions. Plan design is the responsibility of employers in conjunction with their agents (i.e. insurance providers, TPAs, etc.).

Figure 7:
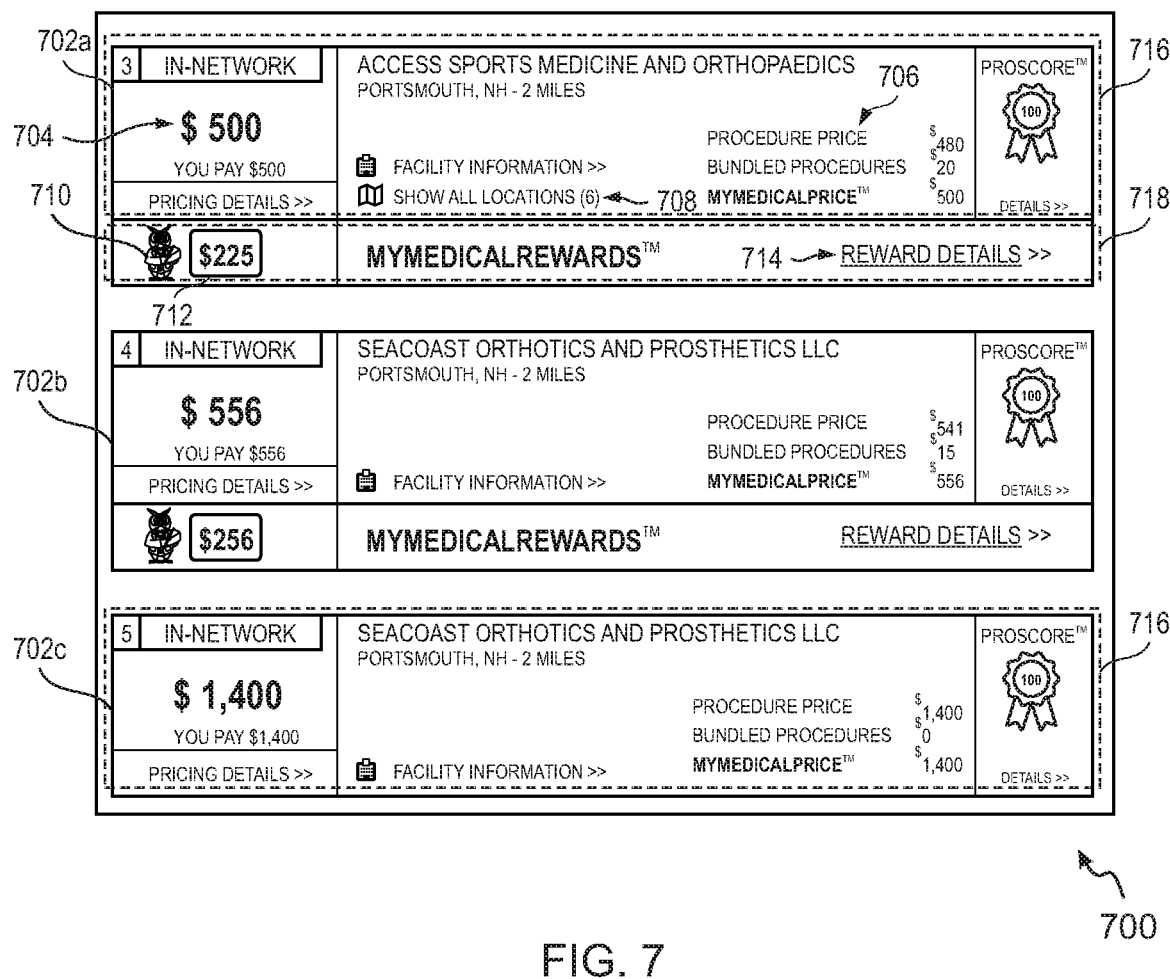
FIG. 7 is an example representation of a UI depicting an employee interface, in accordance with an example embodiment.

FIG. 7 illustrates an example of a UI 700 displaying a list of a plurality of medical service providers available in a predefined region of a location of a user, in accordance with an example embodiment of the present disclosure. The UI 700 is presented to the user (e.g. the employee 102*a*) who wants to avail a medical service. Further, the UI 700 may be displayed in response to employee preference inputs provided by the employee in the healthcare cost management application 112. The employee preference inputs include a location of the employee and at least one medical service required by the user. In some embodiments, the employee may provide a preferred location for availing at least one medical service. Alternatively, the employee may invoke the healthcare cost management application 112 to track a current location of the employee and determine a plurality of medical service providers in the predefined region of the location. In at least one example embodiment, either the employer or the employee can set the predefined region. For example, 5 miles from a current/preferred location provided by the employee. The UI 700 may be an example of the employee interface 120 of FIG. 1.

The UI 700 displays a list of the medical service providers available in the predefined region of the location of the user. The plurality of medical service providers included in the list may provide the medical service required by the user. As shown in the FIG. 7, the list includes three medical service providers 702*a,* 702*b* and 702*c*. It shall be noted that the list has been shown for exemplary purposes and the list may include fewer or more entries than those depicted in FIG. 7.

A price field 704 shown for the medical service provider 702*a* indicates a pricing for the medical service offered by the medical service provider 702*a*. A detailed information field 706 provides a breakdown of the pricing of the medical service charged by the service provider 702*a*. A tab 708 associated with text 'SHOW ALL LOCATIONS' provide details/addresses of the locations at which branches of the medical service provider 702a are available. The user can avail medical service at any branch of the medical service provider 702a as per his/her convenience. An icon 710 represents a reward for selecting the medical service provider 702a. It shall be noted that the icon 710 is presented when a medical service provider provides a medical service requested by the user at a pricing lesser than a reference pricing determined by the employer. In this example representation, reward details are provided beside the icon 710 in a reward field 712. The reward field 712 indicates a monetary value of the reward that may be credited to an account of the user if he/she uses medical services provided by the service provider 702a. A tab 714 associated with text 'REWARD DETAIL' may redirect the user to a page providing details of the rewards program selected by an employer of the user. As shown in FIG. 7, a procedure price section 716 provides details of medical service/procedure pricing offered by the service provider 702a and a reward details section 718 provides corresponding rewards incentive if the medical service is availed from that medical service provider. As shown in the example representation, the pricing of the medical service offered by the medical service provider 702a will be $500 and the value of the rewards that can be earned by the user will be $225 if he/she avails the services from the medical service provider 702a.

In an embodiment, if the pricing offered by a medical service provider is greater than a reference pricing set for that medical service, then the employer provides no reward incentives to the employee if he chooses to avail medical services from that corresponding medical service provider. Hence, the reward details section 718 may not be displayed for the medical service provider whose pricing is greater than the reference pricing (see, medical service provider 702c). For example, the service provider 702c is charging $1400 for providing the medical service whereas a reference pricing is set at $1000, hence a reward details section is not displayed for the service provider 702c in the UI 700.

Figure 8A:
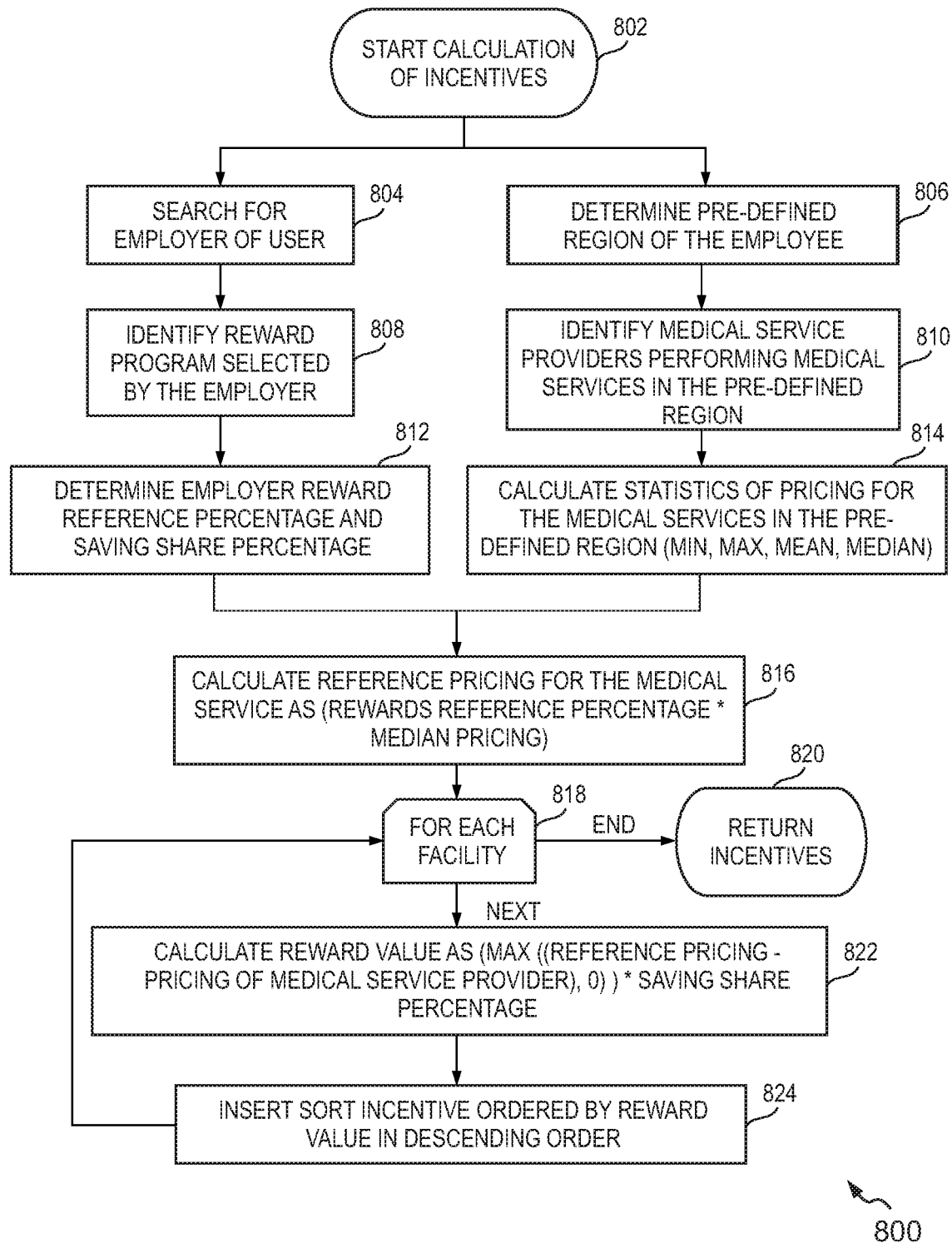
FIG. 8A illustrates a flow diagram of a method for managing healthcare costs, in accordance with an example embodiment.

FIG. 8A illustrates a method 800 for calculating medical rewards incentive, in accordance with an example embodiment.

At step 802, incentive calculation starts.

At step 804, an employer of the user is searched using a look up table.

At step 808, reward program selected by the employer (identified at step 804) is identified using another look up table.

At step 812, employer rewards reference percentage and savings share percentage are determined from the reward program of the employer. The employer configures the details. The output of step 812 is then provided to step 816 for further calculations.

At step 806, a predefined region of the employee is determined. A region can be determined/calculated through a variety of means including but not limited to zip code specification, primary address specification, automatic geolocation via GPS, and specification/selection via a user interface.

At step 810, medical service providers performing medical service (requested by the user) in the predefined region of the user are identified using a look up table.

At step 814, statistics of the pricing for the medical service (by the medical service providers) in the predefined region are calculated. The calculations include determining minimum, maximum, mean and median of the pricing in the predefined region for the medical service/procedure.

The output of step 814 is processed along with output of step 812, at step 816, to calculate reference pricing for the medical service in that predefined region as rewards reference percentage offered by employer*median.

In some embodiments, the calculation is done for each medical service provider providing the medical service in the predefined region of the user. At step 818, it is checked if the calculations are done for all medical service providers in the predefined region. If yes, then incentives are returned at step 820. Else, at step 822, for each medical service provider, a reward value is calculated as (max ((reference pricing−pricing of medical service provider), 0))*savings share percentage.

At step 824, the reward values of the medical service providers are insertion sorted (e.g., by using insertion sort algorithm) in descending order and processing for each medical service provider continues at 818.

Figure 8B:
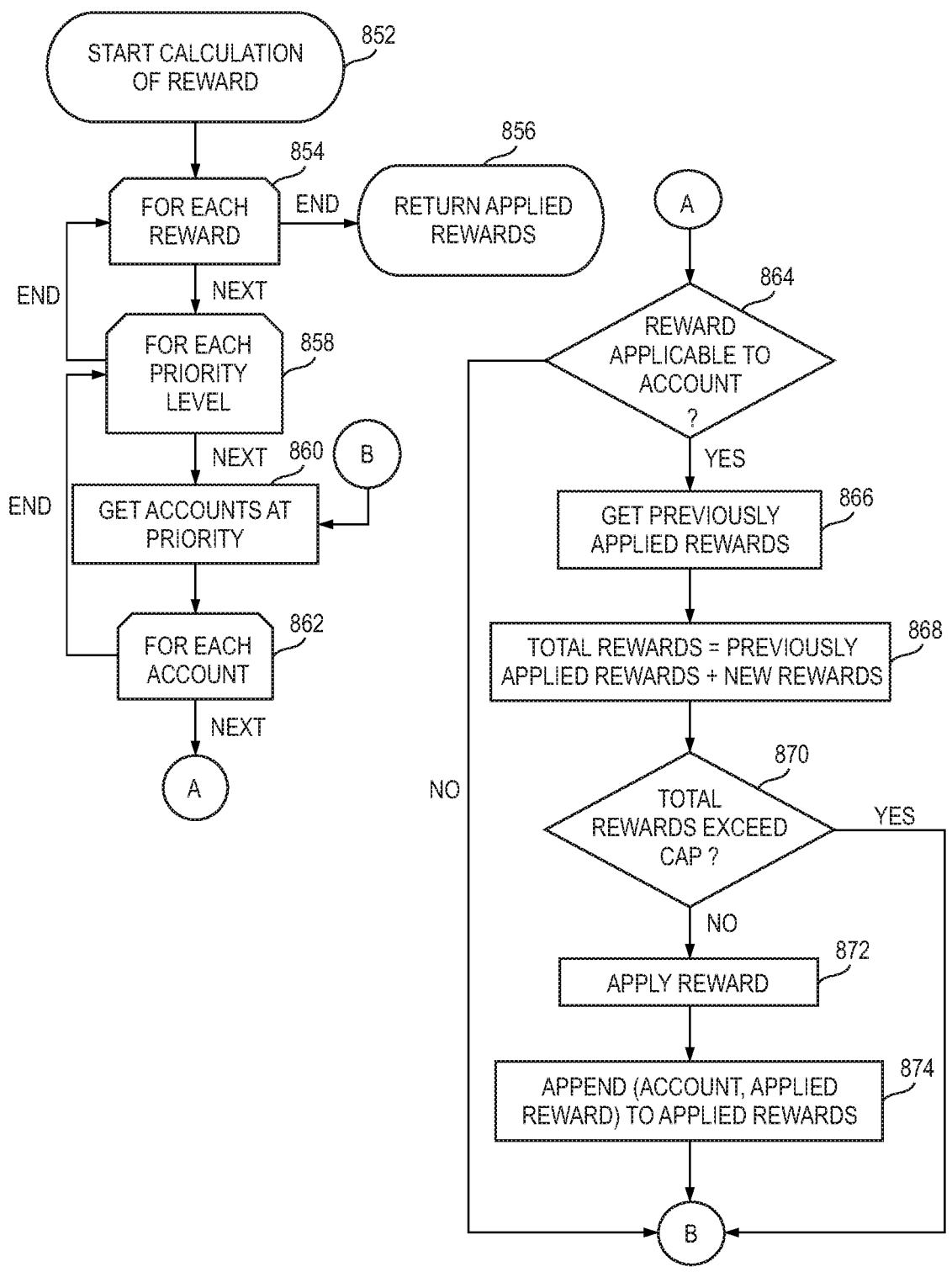
FIG. 8B illustrates a flow diagram of a method for managing healthcare costs, in accordance with an example embodiment.

The reward incentives for each (medical service, medical service provider) pair are obtained in FIG. 8A. These are presented to a user in an employee interface (see, 120), thereby allowing the user to determine which medical service provider to visit. An example of a UI depicting employee interface displaying medical service providers, associated pricing and reward values is shown in FIG. 7. When the healthcare consumer (user/employee) visits a medical service provider to obtain those services, the earned reward(s) for those medical services are determined for that medical service provider. FIG. 8B provides a process explaining how those reward(s) are applied to one or more accounts based on account prioritization and reward limits per account. This process is directed based on program design and legal constraints.

FIG. 8B illustrates a method 850 for managing healthcare costs, in accordance with an example embodiment.

At step 852, reward calculation is started. Reward calculation determines what rewards can be applied to one or more accounts of a user, an order in which the reward is to be applied to the accounts, and an amount to be applied to the accounts.

At step 854, a check is made if all rewards are calculated. If yes, then the rewards are outputted at step 856. Else, for each reward to be applied, a priority level is determined at step 858. A set of priority levels is used to prioritize the application of rewards to the one or more accounts of the user. At each priority level (say 1-4), there may be associated accounts. These accounts are selected by priority level and then iterated over to determine if/how the reward is applied to the account.

If no priority level is left then the method moves to step 856, else step 860 is performed to get accounts at priority. Accounts are assigned a priority level, where this priority level determines the order of rewards application.

At step 862, each account of the one or more accounts is checked. If no account is there or all of the accounts are checked, then method moves to step 858, else at step 864 a check is performed to determine if reward is applicable to the account. If the reward is not application to the account, then method moves to step 860, else previously applied rewards are fetched at step 866.

At step 868, rewards are calculated by summing previously applied rewards and the new rewards determined.

At step 870, a check is performed to determine if total rewards cap is exceeded. If yes, then no further additions are done and the method moves to step 860, else at step 872 the reward is applied, and at step 874 (account, applied reward) is appended to the applied rewards.

Figure 9:
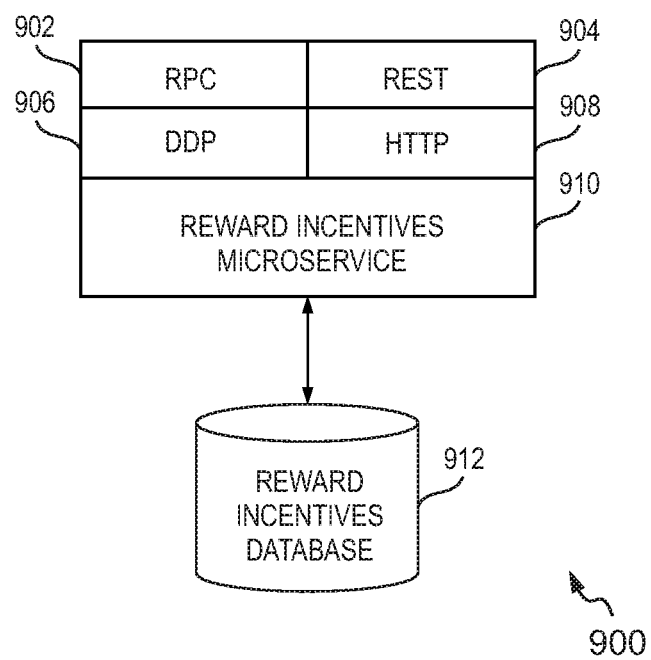
FIG. 9 is a representation of a system for supporting rewards incentives micro service, in accordance with an example embodiment.

FIG. 9 illustrates a system 900 for supporting a reward incentives micro service 910, in accordance with an example embodiment of the present disclosure. The reward incentives micro service 910 can be embodied in the server 110. In an embodiment, a reward incentive can be calculated/retrieved upon request, thereby minimizing the data transferred (i.e. only the result set is returned) at the expense of some additional latency. This is achieved using a rewards incentives database 912.

The rewards incentives micro service 910 supports a number of protocols. As seen in the FIG. 9, a Remote Procedure Call (RPC) 902 over a Distributed Data Protocol (DDP) 906, and a Representational State Transfer (REST) 904 over a Hyper Text Transfer Protocol (HTTP) 908, are supported by the rewards incentives micro service 910. The system 900 is a part of the server 110.

FIG. 10 illustrates a table 1000 indicative of a method followed by the rewards incentives micro service 910, in accordance with an example embodiment of the present disclosure. The table 1000 indicates the method for getting reward incentives and support parameters.

The table 1000 includes fields such as a service name field 1002, a direction field 1004, a name field 1006, a type field 1008, a status field 1010, a default field 1012 and a description field 1014. The service name field 1002 is indicative of a service requested by the reward incentive micro service 910. The direction field 1004 represents if the service requested by the reward incentive micro service 910 is a request/response from the reward incentive micro service 910. The name field 1006 indicates a field identifier defined by a specific name (see, 1006) and the type field 1008 represents data type of the field identifier of the name field 1006. The status field 1010 indicates if the field identifier is required or not for a request/response from/to the reward incentive micro service 910. The default field 1012 includes default values that are pre-set while configuring the reward incentive micro service 910 and the description field 1014 provides a brief description of the field identifier. As shown in the FIG. 10, the rewards incentives micro service 910 may request an identifier of a user in form of 'USER ID', a procedure code to get incentives for the medical service/procedure requested by the employee in the form of 'PROCEDURE CODE', a location of the employee in which the employee wants to avail medical service in the form of 'LOCATION Longitude Latitude (LONLAT)', a predefined region set by the employee in which the employee wants to avail medical service or a radius distance from the location in form of 'RADIUS METERS', a start time to get latest incentives in form of START TIME in Millisecond (MS), and a duration till which the incentive is valid or expiry time in form of DURATION (MS). A response comprising a list of matching reward incentives may be received for the request made by the rewards incentives micro service 910. As shown in the FIG. 10, the rewards incentives may be in form of 'STRING' (e.g., a list of reward incentives in json format), for example, MyMedicalRewards or coupons associated with each service provider. The response is MANDATORY and may be an empty list in the case where no reward incentives are found.

Figure 11:
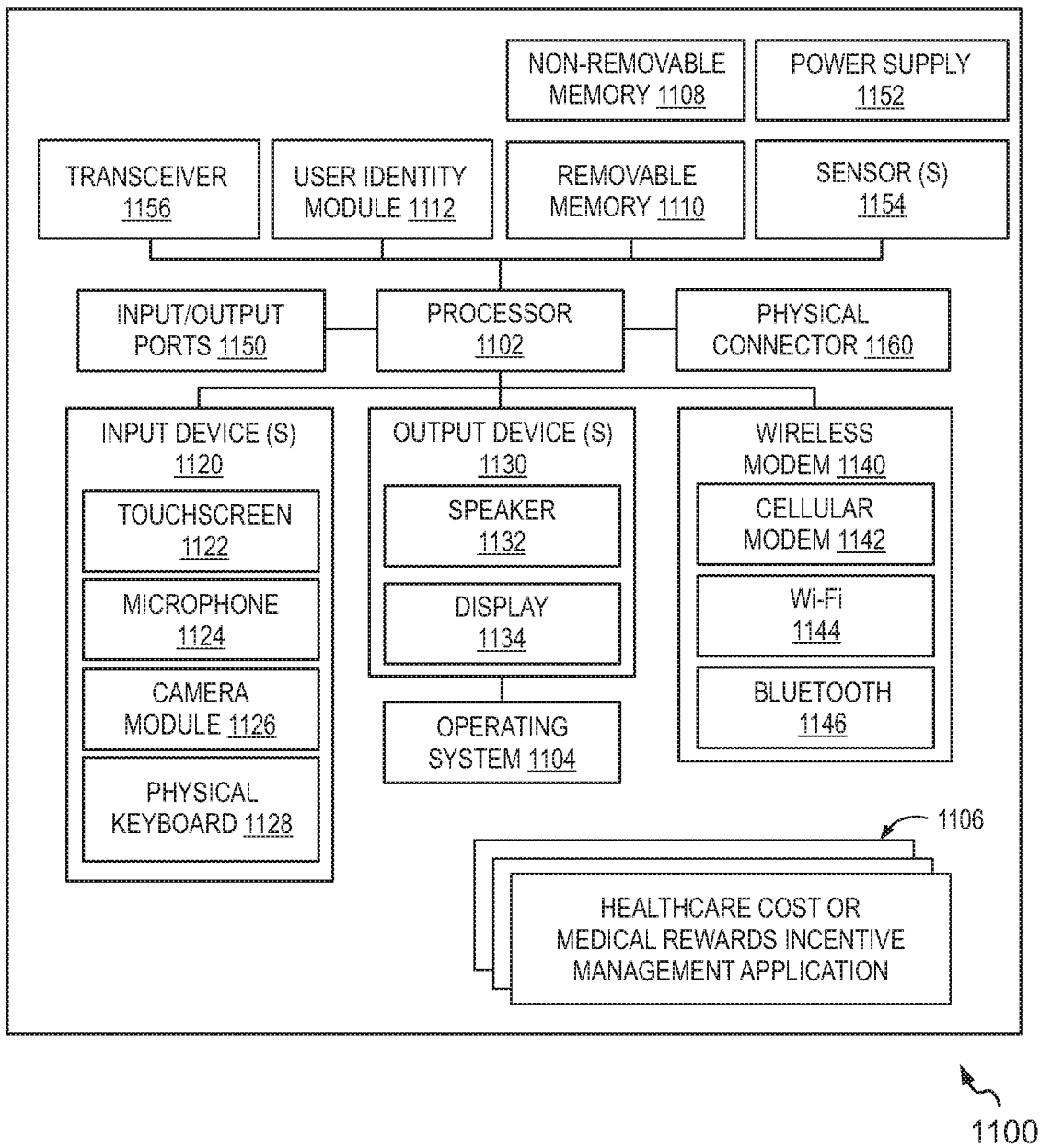
FIG. 11 is a block diagram of an electronic device, in accordance with an example embodiment.

FIG. 11 shows a simplified block diagram of an electronic device 1100 capable of implementing the various embodiments of the present disclosure. The electronic device 1100 may be an example of the electronic devices 104a, 104b and 108. In an embodiment, the various operations related to managing healthcare costs can be facilitated using a healthcare costs management application installed in the electronic device 1100 therein. It should be understood that the electronic device 1100 as illustrated and hereinafter described is merely illustrative of one type of device and should not be taken to limit the scope of the embodiments. As such, it should be appreciated that at least some of the components described below in connection with that the electronic device 1100 may be optional and thus in an example embodiment may include more, less or different components than those described in connection with the example embodiment of the FIG. 11. As such, among other examples, the electronic device 1100 could be any of a mobile electronic device or may be embodied in any of the electronic devices, for example, cellular phones, tablet computers, laptops, mobile computers, personal digital assistants (PDAs), mobile televisions, mobile digital assistants, or any combination of the aforementioned, and other types of communication or multimedia devices.

The illustrated electronic device 1100 includes a controller or a processor 1102 (e.g., a signal processor, microprocessor, ASIC, or other control and processing logic circuitry) for performing such tasks as signal coding, data processing, image processing, input/output processing, power control, and/or other functions. An operating system 1104 control the allocation and usage of the components of the electronic device 1100 and support for one or more applications programs (see, the healthcare costs management application 112) that implements one or more of the innovative features described herein. The applications 1106 may include common mobile computing applications (e.g., telephony applications, email applications, calendars, contact managers, web browsers, messaging applications such as USSD messaging or SMS messaging or SIM Tool Kit (STK) application) or any other computing application. The healthcare costs management application is configured to be in operative communication with other applications for example, through the OS or using API Calls, for managing or reducing the overall healthcare expenditure.

The illustrated electronic device 1100 includes one or more memory components, for example, a non-removable memory 1108 and/or a removable memory 1110. The non-removable memory 1108 and/or the removable memory 1110 may be collectively known as database in an embodiment. The non-removable memory 1108 can include RAM, ROM, flash memory, a hard disk, or other well-known memory storage technologies. The removable memory 1110 can include flash memory, smart cards, or a Subscriber Identity Module (SIM). The one or more memory components can be used for storing data and/or code for running the operating system 1104 and the healthcare costs or medical rewards management. The electronic device 1100 may further include a user identity module (UIM) 1112. The UIM 1112 may be a memory device having a processor built in. The UIM 1112 may include, for example, a subscriber identity module (SIM), a universal integrated circuit card (UICC), a universal subscriber identity module (USIM), a removable user identity module (R-UIM), or any other smart card. The UIM 1112 typically stores information elements related to a mobile subscriber. The UIM 1112 in form of the SIM card is well known in Global System for Mobile Communications (GSM) communication systems, Code Division Multiple Access (CDMA) systems, or with third-generation (3G) wireless communication protocols such as Universal Mobile Telecommunications System (UMTS), CDMA9000, wideband CDMA (WCDMA) and time division-synchronous CDMA (TD-SCDMA), or with fourth-generation (4G) wireless communication protocols such as LTE (Long-Term Evolution).

The electronic device 1100 can support one or more input devices 1120 and one or more output devices 1130. Examples of the input devices 1120 may include, but are not limited to, a touch screen/a display screen 1122 (e.g., capable of capturing finger tap inputs, finger gesture inputs, multi-finger tap inputs, multi-finger gesture inputs, or keystroke inputs from a virtual keyboard or keypad), a microphone 1124 (e.g., capable of capturing voice input), a camera module 1126 (e.g., capable of capturing still picture images and/or video images) and a physical keyboard 1128. Examples of the output devices 1130 may include, but are not limited to a speaker 1132 and a display 1134. Other possible output devices can include piezoelectric or other haptic output devices. Some devices can serve more than one input/output function. For example, the touch screen 1122 and the display 1134 can be combined into a single input/output device.

A wireless modem 1140 can be coupled to one or more antennas (not shown in the FIG. 11) and can support two-way communications between the processor 1102 and external devices, as is well understood in the art. The wireless modem 1140 is shown generically and can include, for example, a cellular modem 1142 for communicating at long range with the mobile communication network, a Wi-Fi compatible modem 1144 for communicating at short range with an external Bluetooth-equipped device or a local wireless data network or router, and/or a Bluetooth-compatible modem 1146. The wireless modem 1140 is typically configured for communication with one or more cellular networks, such as a GSM network for data and voice communications within a single cellular network, between cellular networks, or between the electronic device 1100 and a public switched telephone network (PSTN).

The electronic device 1100 can further include one or more input/output ports 1150, a power supply 1152, one or more sensors 1154 for example, an accelerometer, a gyroscope, a compass, or an infrared proximity sensor for detecting the orientation or motion of the electronic device 1100, a transceiver 1156 (for wirelessly transmitting analog or digital signals) and/or a physical connector 1160, which can be a USB port, IEEE 1294 (FireWire) port, and/or RS-232 port. The illustrated components are not required or all-inclusive, as any of the components shown can be deleted and other components can be added.

The disclosed systems and methods with reference to FIGS. 1 to 12, or one or more operations of the flow diagrams may be implemented using software including computer-executable instructions stored on one or more computer-readable media (e.g., non-transitory computer-readable media, such as one or more optical media discs, volatile memory components (e.g., DRAM or SRAM), or non-volatile memory or storage components (e.g., hard drives or solid-state non-volatile memory components, such as Flash memory components) and executed on a computer (e.g., any suitable computer, such as a laptop computer, net book, Web book, tablet computing device, smart phone, or other mobile computing device). Such software may be executed, for example, on a single local computer or in a network environment (e.g., via the Internet, a wide-area network, a local-area network, a remote web-based server, a client-server network (such as a cloud computing network), or other such network) using one or more network computers. Additionally, any of the intermediate or final data created and used during implementation of the disclosed methods or systems may also be stored on one or more computer-readable media (e.g., non-transitory computer-readable media) and are considered to be within the scope of the disclosed technology. Furthermore, any of the software-based embodiments may be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

FIG. 12 is a simplified block diagram of a server system 1200, for managing healthcare costs, in accordance with one embodiment of the present disclosure. The server system 1200 is an example of the server 110 shown and explained with reference to FIG. 1. The server system 1200 includes a computer system 1202 and one or more database, such as a database 1204.

The computer system 1202 includes a processor 1206 for executing instructions. Instructions may be stored in, for example, but not limited to, a memory 1208. The processor 1206 may include one or more processing units (e.g., in a multi-core configuration). The processor 1206 is operatively coupled to a communication interface 1210 such that the computer system 1202 is capable of communicating with a remote device such as an electronic device 1220. Some examples of the electronic device 1220 may include, but are not limited to, the electronic devices 104a, 104b and 108 shown in FIG. 1.

The processor 1206 may also be operatively coupled to the database 1204. The database 1204 is configured to store the healthcare costs management application 112 capable of enabling a user to manage healthcare costs as explained with reference to FIGS. 1 to 10. The database 1204 is any computer-operated hardware suitable for storing and/or retrieving data. The database 1204 may include multiple storage units such as hard disks and/or solid-state disks in a redundant array of inexpensive disks (RAID) configuration. The database 1204 may include, but not limited to, a storage area network (SAN) and/or a network attached storage (NAS) system.

In some embodiments, the database 1204 is integrated within the computer system 1202. For example, the computer system 1202 may include one or more hard disk drives as the database 1204. In other embodiments, the database 1204 is external to the computer system 1202 and may be accessed by the computer system 1202 using a storage interface 1212. The database 1204 may be configured to store tables, such as, table 500, table 520, table 540 or table 560 for hosting and managing information related to employers, reward programs, reward incentives and rewards. Further, the database 1204 includes a plurality of employee records that comprise information about healthcare expenditures, claims, settlements, reward incentives received by employees and the like. The storage interface 1212 is any component capable of providing the processor 1206 with access to the database 1204. The storage interface 1212 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing the processor 1206 with access to the database 1204.

The memory 1208 is a storage device embodied as one or more volatile memory devices, one or more non-volatile memory devices, and/or a combination of one or more volatile memory devices and non-volatile memory devices, for storing micro-contents information and instructions. The memory 1208 may be embodied as magnetic storage devices (such as hard disk drives, floppy disks, magnetic tapes, etc.), optical magnetic storage devices (e.g., magneto-optical disks), CD-ROM (compact disc read only memory), CD-R (compact disc recordable), CD-R/W (compact disc rewritable), DVD (Digital Versatile Disc), BD (Blu-ray® Disc), and semiconductor memories (such as mask ROM, PROM (programmable ROM), EPROM (erasable PROM), flash ROM, RAM (random access memory), etc.,).

The processor 1206 is configured to receive employee preference inputs from an employee for accessing medical services in a predefined region of a location provided by the employee. The processor 1206 is further configured to perform one or more functions such as, accessing a plurality of pricing from a plurality of medical service providers in the predefined region, determining a median pricing for the medical service in the predefined region, accessing a reward program selected by an employer for the medical services, determining a reference pricing for the medical service in the predefined region, computing a differential pricing between the reference pricing and a pricing of each of the medical service providers, determining a reward incentive for each medical service provider based on the differential pricing and displaying each medical service provider of the plurality of medical service providers in the predefined region along with an associated pricing and reward incentive for availing the medical service. Thereafter, the processor 1206 is further configured to determine a reward for the employee based on selection of a medical service provider for availing the medical service based on the reward program selected by the employer.

Although the invention has been described with reference to specific exemplary embodiments, it is noted that various modifications and changes may be made to these embodiments without departing from the broad spirit and scope of the invention. For example, the various operations, blocks, etc., described herein may be enabled and operated using hardware circuitry (for example, complementary metal oxide semiconductor (CMOS) based logic circuitry), firmware, software and/or any combination of hardware, firmware, and/or software (for example, embodied in a machine-readable medium). For example, the apparatuses and methods may be embodied using transistors, logic gates, and electrical circuits (for example, application specific integrated circuit (ASIC) circuitry and/or in Digital Signal Processor (DSP) circuitry).

The present disclosure is described above with reference to block diagrams and flowchart illustrations of method and system embodying the present disclosure. It will be understood that various block of the block diagram and flowchart illustrations, and combinations of blocks in the block diagrams and flowchart illustrations, respectively, may be implemented by a set of computer program instructions. These set of instructions may be loaded onto a general-purpose computer, special purpose computer, or other programmable data processing apparatus to cause a device, such that the set of instructions when executed on the computer or other programmable data processing apparatus create a means for implementing the functions specified in the flowchart block or blocks. Although other means for implementing the functions including various combinations of hardware, firmware and software as described herein may also be employed.

Various embodiments described above may be implemented in software, hardware, application logic or a combination of software, hardware and application logic. The software, application logic and/or hardware may reside on at least one memory, at least one processor, an apparatus or, a non-transitory computer program product. In an example embodiment, the application logic, software or an instruction set is maintained on any one of various conventional computer-readable media. In the context of this document, a "computer-readable medium" may be any non-transitory media or means that can contain, store, communicate, propagate or transport the instructions for use by or in connection with an instruction execution system, apparatus, or device, such as a computer. A computer-readable medium may comprise a computer-readable storage medium that may be any media or means that can contain or store the instructions for use by or in connection with an instruction execution system, apparatus, or device, such as a computer.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The embodiments were chosen and described in order to best explain the principles of the present disclosure and its practical application, to thereby enable others skilled in the art to best utilize the present disclosure and various embodiments with various modifications as are suited to the particular use contemplated. It is understood that various omissions and substitutions of equivalents are contemplated as circumstance may suggest or render expedient, but such are intended to cover the application and\or implementation without departing from the spirit or scope of the claims.

What is claimed is:

1. A method, comprising:
receiving, by a processor, one or more employee preference inputs from an employee for accessing medical services, the one or more employee preference inputs comprising:
at least one medical service, and
a location of the employee;
accessing, by the processor, a plurality of pricing from a plurality of medical service providers in a predefined region of the location for the at least one medical service, wherein the plurality of pricing in the predefined region is used for determining a median pricing for the at least one medical service;
accessing, by the processor, a reward program selected by an employer of the employee for the medical services, the reward program comprising at least:
a reward reference percentage, wherein the reward reference percentage is a percentage for every medical service availed below a reference pricing,
a savings share percentage, wherein the savings share percentage is at least a part of a savings of the employer based on a pricing for the at least one medical service, and
a reward incentive limiting value defining a maximum reward incentive to be offered to the employee;
determining, by the processor, the reference pricing for the at least one medical service based on the reward reference percentage and the median pricing, wherein determining the reference pricing for the at least one medical service comprises calculating the reference pricing by multiplying the reward reference percentage and the median pricing for the at least one medical service;
determining, by the processor, a differential pricing for each medical service provider of the plurality of medical service providers by comparing the reference pricing with a corresponding pricing offered by each of the medical service providers for the at least one medical service;

calculating, by the processor, a reward incentive for each of the medical service provider to be offered to the employee based on the differential pricing and the savings share percentage for the at least one medical service;

determining, by the processor, whether total rewards offered to the employee is less than the reward incentive limiting value or not, wherein the total rewards is calculated by summing previously applied reward incentives and the reward incentive; and in response to a determination that the total rewards is less than the reward incentive limiting value, appending, by the processor, the reward incentive to an account associated with the employee, wherein the reward incentive is credited to one or more accounts of the employee as per a reward limit based on an account prioritization set by the employer, and wherein the reward limit is the maximum amount that is allowed to credit into each account of the employee based on legal constraints.

2. The method as claimed in claim 1, wherein the reward reference percentage and the savings share percentage are pre-set by the employer.

3. The method as claimed in claim 1, wherein accessing the plurality of pricing from the plurality of medical service providers comprises identifying, by the processor, the plurality of medical service providers providing the at least one medical service in the predefined region of the location of the employee.

4. The method as claimed in claim 1, wherein the reward incentive for each medical service provider of the plurality of medical service providers is determined based on a predefined mathematical expression.

5. The method as claimed in claim 4, wherein the predefined mathematical expression is $X=(\max((A-B), 0)*C$, where X is the reward incentive, A is the reference pricing, B is a pricing offered by a medical service provider of the plurality of medical service provider and C is the savings share percentage.

6. The method as claimed in claim 4, further comprising:
provisioning, by the processor, a user interface (UI) for the employee to provide a selection of at least one medical service provider, the UI comprising a display of:
the plurality of medical service providers in the predefined region;
a pricing associated with each medical service provider of the plurality of medical service providers; and
a reward incentive associated with each medical service provider when the reference pricing is greater than the pricing offered by the medical service provider.

7. The method as claimed in claim 6, further comprising:
facilitating, by the processor, a provision of the reward incentive associated with the medical service provider to the employee based on a set of priority levels, the set of priority levels being defined in the reward program; and
storing, by the processor, the reward incentive for the at least one medical service in an employee record.

8. The method as claimed in claim 7, wherein the one or more accounts comprise:
a health reimbursement arrangement account;
a flexible spending account; and
a health savings account.

9. The method as claimed in claim 8, wherein the reward incentive is an incentive program comprising at least one of:
a loyalty point;
a coupon;
a membership; and
a cash price.

10. The method as claimed in claim 1, wherein calculating the reward incentive further comprises:
sending, by the processor, a request for a reward incentive design to a database; and
upon receiving a request, retrieving the reward incentive design by a reward incentive micro service.

11. The method as claimed in claim 10, wherein the reward incentive micro service supports one or more of:
a Remote Procedure Call (RPC) over Distributed Data Protocol (DDP); and
a Representational State Transfer (REST) over Hyper Text Transfer Protocol (HTTP).

12. A server for managing healthcare costs, comprising:
a memory configured to store instructions; and
a processor configured to execute the instructions stored in the memory and thereby cause the processor to perform:
receiving one or more employee preference inputs from an employee for accessing medical services, the one or more employee preference inputs comprising:
at least one medical service, and
a location of the employee;
accessing a plurality of pricing from a plurality of medical service providers in a predefined region of the location for the at least one medical service, wherein the plurality of pricing in the predefined region is used for determining a median pricing for the at least one medical service;
accessing a reward program selected by an employer of the employee for the medical services, the reward program comprising at least:
a reward reference percentage, wherein the reward reference percentage is a percentage for every medical service availed below a reference pricing,
a savings share percentage, wherein the savings share percentage is at least a part of a savings of the employer based on a pricing for the at least one medical service, and
a reward incentive limiting value defining a maximum reward incentive to be offered to the employee;
determining the reference pricing for the at least one medical service based on the reward reference percentage and the median pricing, wherein determining the reference pricing for the at least one medical service comprises calculating the reference pricing by multiplying the reward reference percentage and the median pricing for the at least one medical service;
determining a differential pricing for each medical service provider of the plurality of medical service providers by comparing the reference pricing with a corresponding pricing offered by each of the medical service providers for the at least one medical service;
calculating a reward incentive for each of the medical service provider to be offered to the employee based on the differential pricing and the savings share percentage for the at least one medical service;
determining whether total rewards offered to the employee is less than the reward incentive limiting value or not, wherein the total rewards is calculated by summing previously applied reward incentives and the reward incentive; and in response to a determination that the total rewards is less than the reward incentive limiting value, appending the reward incentive to an account associated with the employee, wherein the reward incentive is credited to one or more accounts of the employee as per a reward limit based on an account prioritization set by the employer, and wherein the reward limit is the maximum amount that is allowed to credit into each account of the employee based on legal constraints.

13. The server as claimed in claim 12, wherein for determining the reference pricing for the at least one medical service, the processor is further caused to:

identify the employer of the employee; and access the reward program of the employer, the reward program comprising at least the reward reference percentage and the savings share percentage.

14. The server as claimed in claim 12, wherein for accessing the plurality of pricing from the plurality of medical service providers, the processor is further caused to identify the plurality of medical service providers providing the at least one medical service in the predefined region of the location of the employee.

15. The server as claimed in claim 12, wherein the reward incentive for each medical service provider of the plurality of medical service providers is determined based on a predefined mathematical expression.

16. The server as claimed in claim 15, wherein the predefined mathematical expression is $X=(\max((A-B), 0)*C)$, where X is the reward incentive, A is the reference pricing, B is the pricing offered by a medical service provider and C is the savings share percentage.

17. The server as claimed in claim 12, wherein the processor is further caused to provision a UI for the employee to provide a selection of at least one medical service provider, the UI comprising:

the plurality of medical service providers in the predefined region;

a pricing associated with each medical service provider of the plurality of medical service providers; and a reward incentive associated with each medical service provider when the reference pricing is greater than the pricing offered by a medical service provider.

18. The server as claimed in claim 17, wherein the processor is further caused to:

facilitate a provision of the reward incentive associated with the medical service provider to the employee based on a set of priority levels, the set of priority levels being defined in the reward program; and store the reward incentive for the at least one medical service in an employee record.

19. A server system, comprising:

one or more databases configured to store information of a plurality of reward programs offered by an employer, and a plurality of medical service providers; and a computer system comprising a memory configured to store instructions, and a processor configured to execute the instructions stored in the memory and thereby cause the processor to perform:

maintaining records of employees associated with the employer;

calculating a predefined region based on an employee preference input, the employee preference input comprising a medical service opted by an employee and a location of the employee where the employee wants to avail the medical service;

determining a reward reference percentage of the employer and a savings share percentage associated with the employer, wherein the reward reference percentage is a percentage for every medical service availed below a reference pricing;

determining a reward incentive limiting value defining a maximum reward incentive to be offered to the employee;

calculating a median pricing of a plurality of pricing associated with the plurality of medical service providers for the medical service in the predefined region of the employee;

calculating the reference pricing based at least on the median pricing and the reward reference percentage of the employer, wherein calculating the reference pricing comprises performing a multiplication operation between the reward reference percentage and the median pricing for the medical service;

calculating a corresponding reward incentive to the employee for selecting each of a list of medical service providers present in the predefined region;

determining whether total rewards offered to the employee is less than the reward incentive limiting value or not, wherein the total rewards is calculated by summing previously applied reward incentives and the corresponding reward incentive; and in response to a determination that the total rewards is less than the reward incentive limiting value, appending the reward incentive to an account associated with the employee, wherein the reward incentive is credited to one or more accounts of the employee as per a reward limit based on an account prioritization set by the employer, and wherein the reward limit is the maximum amount that is allowed to credit into each account of the employee based on legal constraints.

20. The server system as claimed in claim 19, wherein a reward incentive when the medical service is availed at a medical service provider is determined based at least on a pre-defined mathematical expression $X=(\max((A-B), 0)*C)$, where X is the reward incentive, A is the reference pricing, B is a pricing offered by the medical service provider, and C is the savings share percentage.

\* \* \* \* \*